US006582388B1

(12) United States Patent
Coleman et al.

(10) Patent No.: US 6,582,388 B1
(45) Date of Patent: Jun. 24, 2003

(54) CARDIAC BYPASS CATHETER SYSTEM AND METHOD OF USE

(75) Inventors: Ronald Coleman, Oakland, CA (US); Jeffrey S. Kadan, Redondo Beach, CA (US); Frederick Gotha, Arcadia, CA (US); James C. Peacock, III, Sunnyvale, CA (US)

(73) Assignee: Advanced Interventional Technologies, Inc., Redondo Beach, CA (US)

( * ) Notice: Subject to any disclaimer, the term of this patent is extended or adjusted under 35 U.S.C. 154(b) by 0 days.

(21) Appl. No.: 09/358,247

(22) Filed: Jul. 21, 1999

Related U.S. Application Data

(63) Continuation of application No. 08/976,250, filed on Nov. 21, 1997, now Pat. No. 5,928,181.

(51) Int. Cl.[7] .................. A61M 37/00; A61M 25/00
(52) U.S. Cl. ................. 604/8; 604/96.01; 604/101.01; 604/101.05; 604/919
(58) Field of Search .................. 604/4, 6.1, 6.11, 604/6.16, 8–10, 34, 39–43, 96–104, 194, 619; 128/898

(56) References Cited

U.S. PATENT DOCUMENTS

| 4,592,754 A | * | 6/1986 | Gupte et al. ............... 623/1 |
| 4,836,204 A | * | 6/1989 | Landymore et al. ....... 128/334 |
| 5,267,940 A | * | 12/1993 | Moulder .................... 600/16 |
| 5,403,274 A | * | 4/1995 | Cannon ...................... 604/9 |
| 5,445,600 A | * | 8/1995 | Abdulla ...................... 604/9 |

(List continued on next page.)

Primary Examiner—Angela D. Sykes
Assistant Examiner—Leslie R Deak
(74) Attorney, Agent, or Firm—Frederick Gotha; James C. Peacock, III

(57) ABSTRACT

A medical device assembly is adapted to isolate the heart from systemic circulation while perfusing oxygenated blood to the systemic arterial circulation during a minimally invasive bypasss procedure. An arterial catheter with an external shunt valve forms a funnel which shunts antegrade aortic blood flow from the aortic root, into a distal flow port and through an internal flow lumen in the catheter, out an intermediate flow port along the catheter proximally of the anchor, and into the systemic arterial circulation. A distal internal valve selectively occludes the shunted antegrade aortic blood flow between the distal flow port and the intermediate flow port and isolates the left heart chambers from the systemic arterial circulation. Oxygenated blood may then flow from a cardiopulmonary bypass pump, distally through the internal flow lumen, out the intermediate port. The assembly also includes a venous catheter which aspirates venous blood from the vena cavae and into the cardiopulmonary bypass pump while substantially isolating the right heart chambers from the vena cavae and without circumferentially engaging the internal walls of the vena cavae. Distal and intermediate external valves are positioned along the venous catheter within the superior and inferior vena cava, respectively, and between the sinus venarum into the right atrium and either a distal or intermediate flow port, also respectively. The flow ports communicate with a cardiopulmonary bypass pump through at least one flow lumen through the catheter. Each external valve is adjustable to have an outer diameter which is slightly less than the inner diameter of the respective vena cava so that venous blood is substantially occluded from flowing into the sinus venarum and is instead aspirated into the adjacent flow port.

33 Claims, 18 Drawing Sheets

U.S. PATENT DOCUMENTS

| | | | | |
|---|---|---|---|---|
| 5,584,803 A | * | 12/1996 | Stevens et al. | 604/4 |
| 5,655,548 A | * | 8/1997 | Nelson et al. | 128/898 |
| 5,662,711 A | * | 9/1997 | Douglas | 623/12 |
| 5,725,496 A | * | 3/1998 | Peters | 604/49 |
| 5,746,709 A | * | 5/1998 | Rom et al. | 604/12 |
| 5,755,682 A | * | 5/1998 | Knudson et al. | 604/8 |
| 5,810,757 A | * | 9/1998 | Sweezer, Jr. et al. | 604/4 |
| 5,824,055 A | * | 10/1998 | Spiridigliozzi et al. | 623/1 |
| 5,824,071 A | * | 10/1998 | Nelson et al. | 623/3 |
| 5,827,220 A | * | 10/1998 | Runge | 604/49 |
| 5,827,237 A | * | 10/1998 | Macoviak et al. | 604/246 |
| 5,833,671 A | * | 11/1998 | Macoviak et al. | 604/247 |
| 5,928,181 A | * | 7/1999 | Coleman et al. | 604/8 |
| 6,139,517 A | * | 10/2000 | Macoviak et al. | 604/8 |
| 6,165,162 A | * | 12/2000 | Safar et al. | 604/508 |
| 6,210,365 B1 | * | 4/2001 | Afzal | 604/101.03 |

* cited by examiner

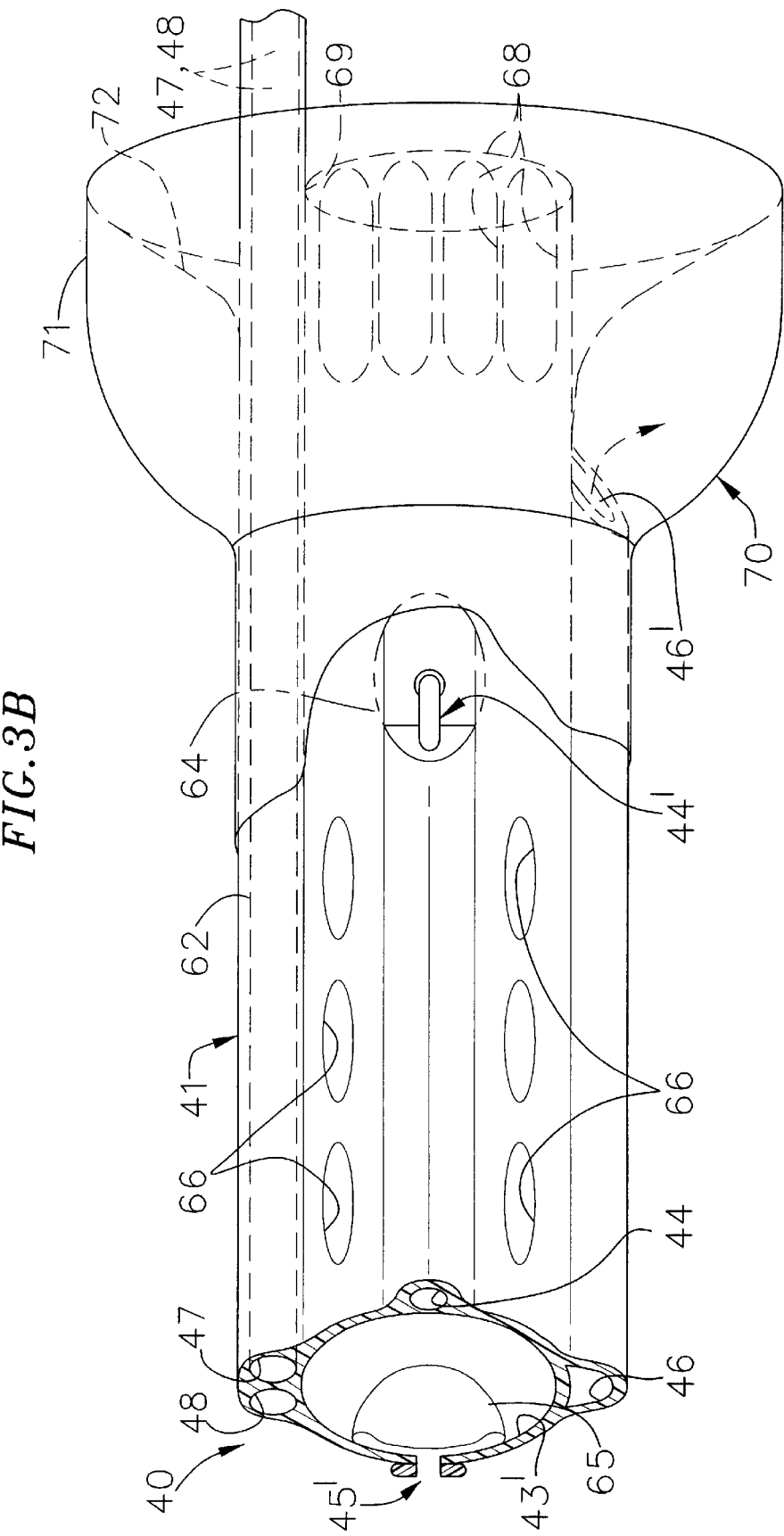

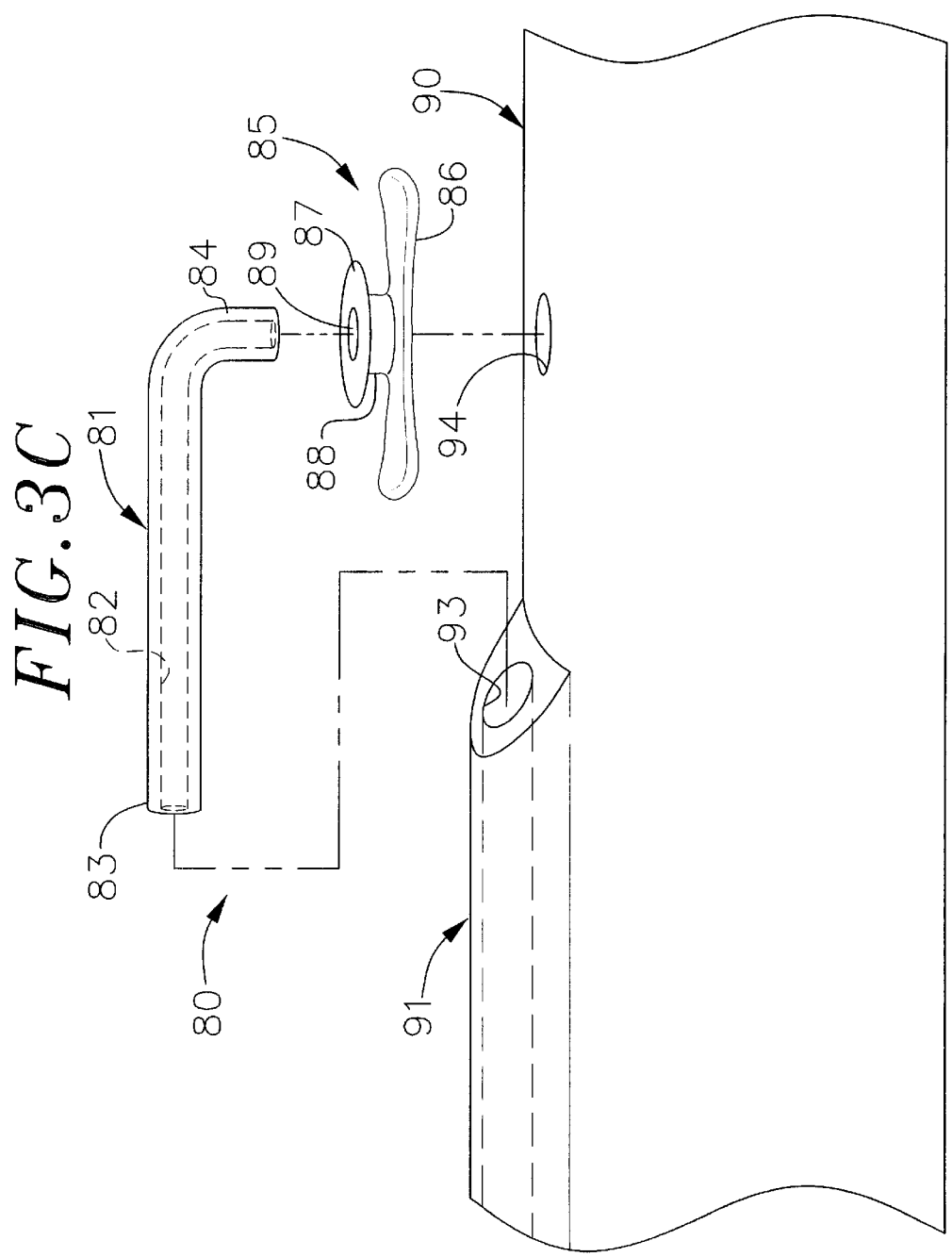

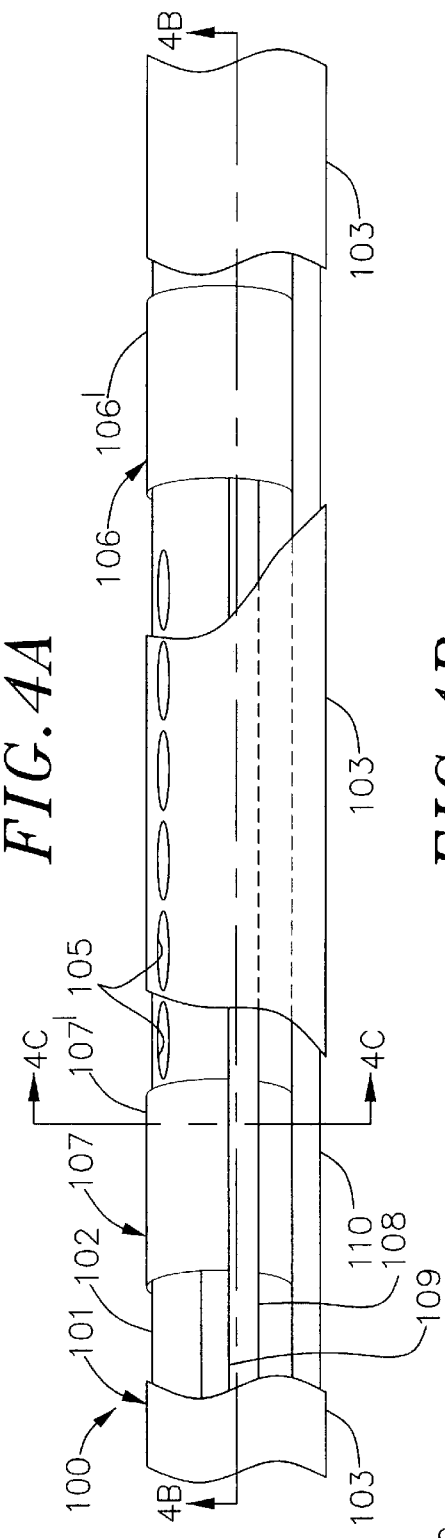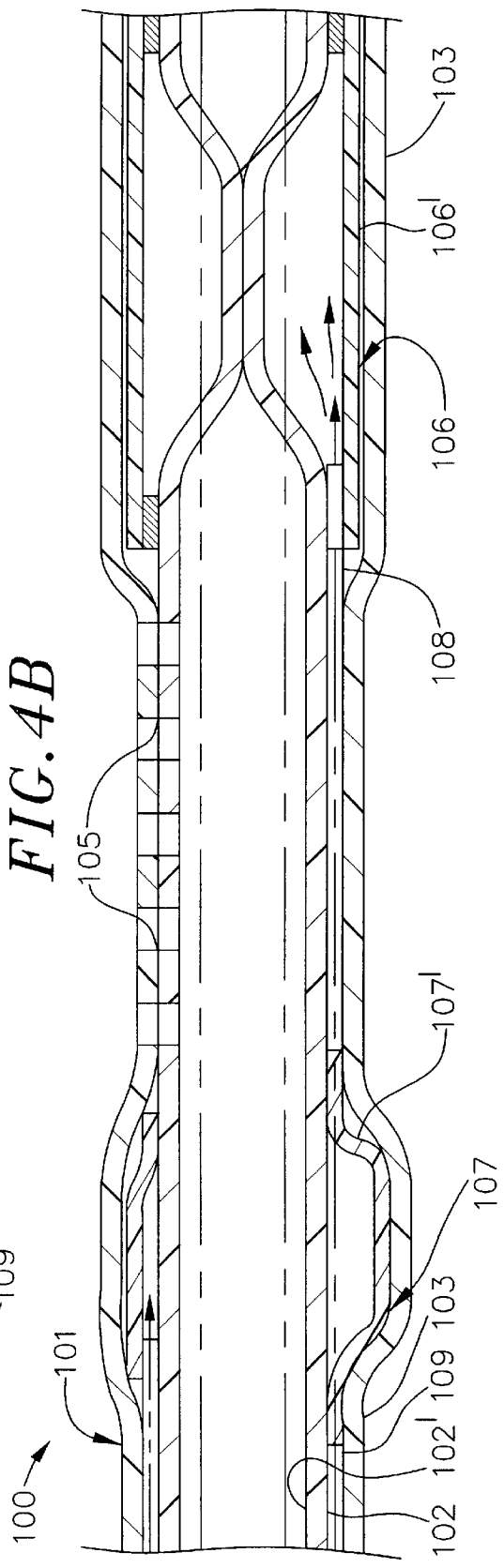
FIG. 4A
FIG. 4B

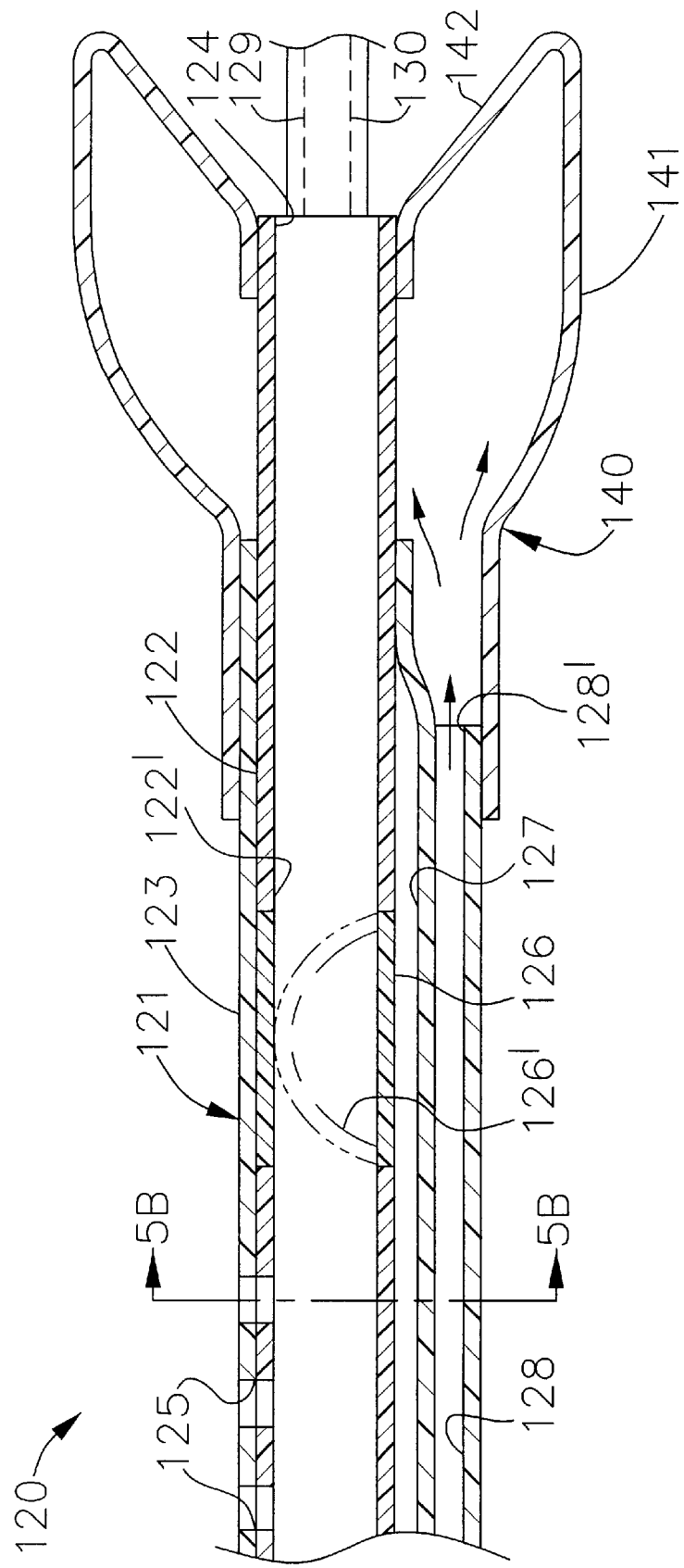

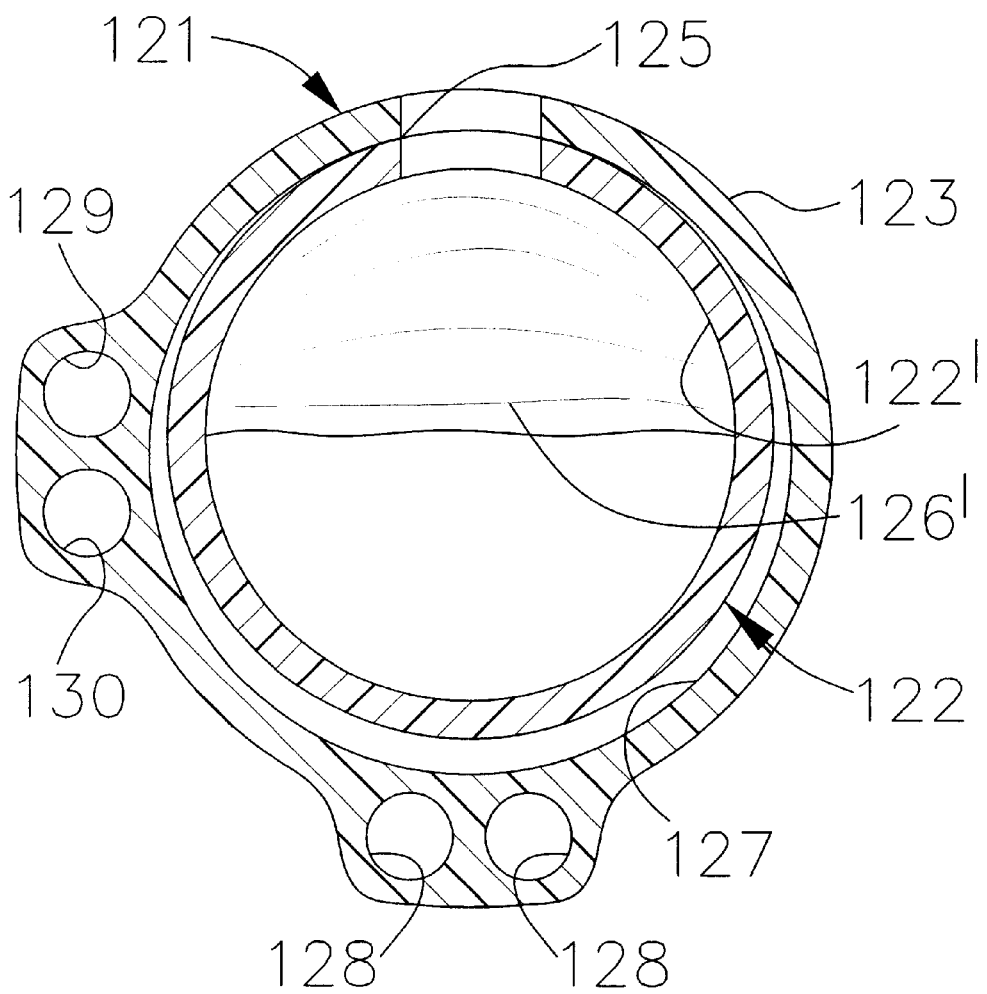

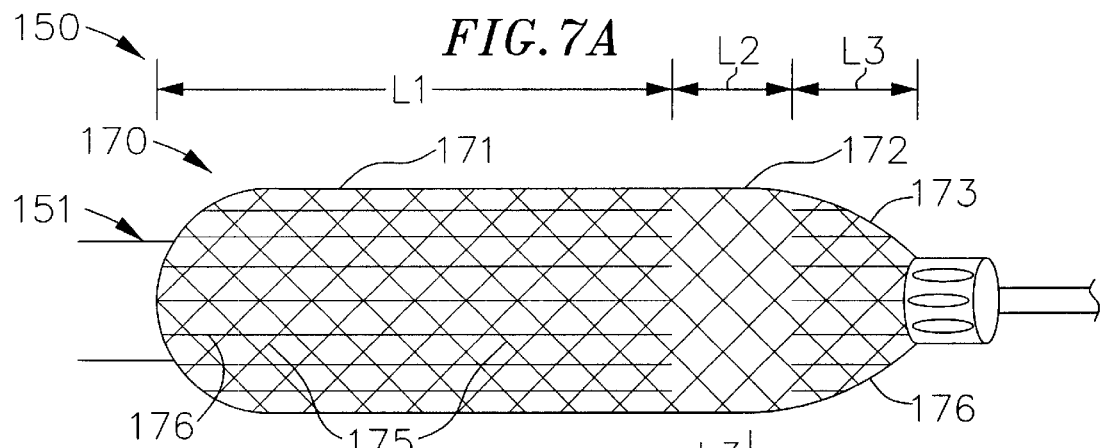
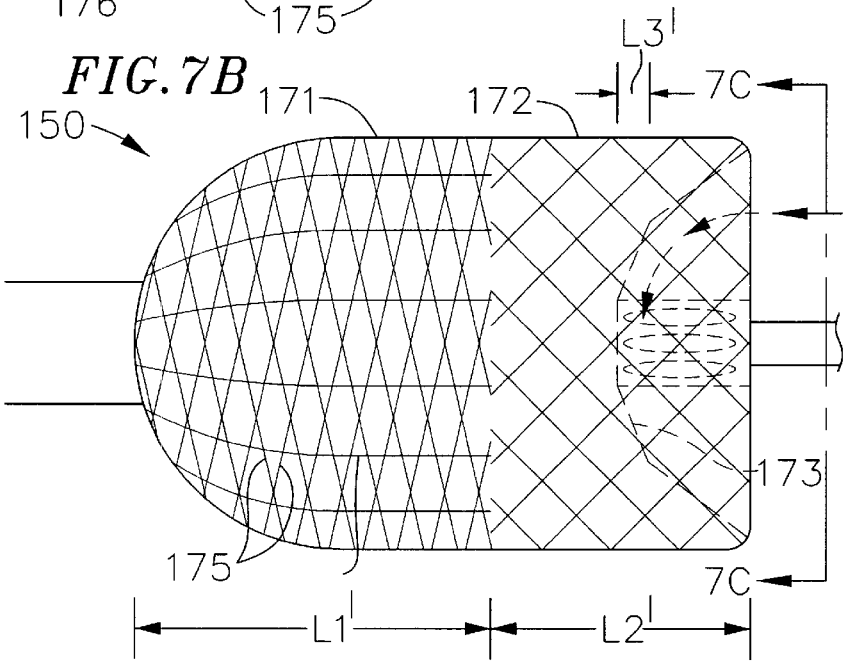
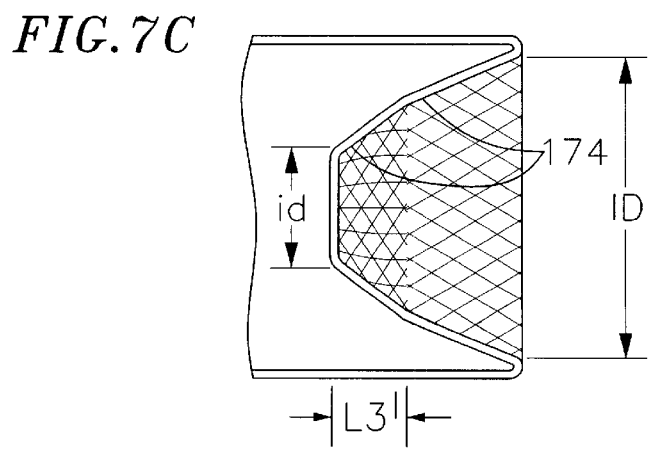

CARDIAC BYPASS CATHETER SYSTEM AND METHOD OF USE

This is a Continuation of application Ser. No. 08/976,250 filed Nov. 21, 1997 now U.S. Pat. No. 5,928,181.

TECHNICAL FIELD

The present invention is a surgical device assembly. More particularly, it is a catheter system which is adapted to provide artificial systemic blood circulation while temporarily arresting the heart and substantially isolating the heart from the systemic circulation in order to perform surgical procedures on the heart.

BACKGROUND

Various abnormalities of the heart are generally treated by temporarily arresting the heart from beating, isolating the heart from systemic blood circulation, supporting the systemic blood circulation via an external cardiopulmonary bypass pump, and performing surgical operations directly on the stopped heart. This general method is herein referred to as a "cardiac bypass procedure". Examples of such cardiac bypass procedures include, without limitation: coronary artery bypass graft surgery ("CABG"); valve replacement surgery; cardiac transplantation surgery; and a procedure known as the "maze" procedure wherein conduction blocks are surgically formed in the wall of one or both of the atria in order to prevent atrial fibrillation.

Conventional techniques in performing such "cardiac bypass procedures" generally include cutting through the sternum in the chest cavity using well known "sternotomy" techniques, spreading open the rib cage, retracting the lungs from the region of the heart, and directly exposing the heart to the surgeon. One of various known cardioplegia agents may be used to temporarily arrest the heart from beating. Further to the bypass procedure, an external cross clamp is generally used to occlude the aorta in the region of the arch between the aortic root and the carotid arteries. With the cross-clamp in this position, both the left heart chambers and the coronary arteries into the heart are isolated from the systemic arterial circulation while the carotid arteries are fed with the blood flow from the bypass pump. In addition, flow from the superior and inferior vena cava is also temporarily diverted from the heart to the pump, usually by externally tying the vena caval walls onto venous pump cannulae.

Minimally Invasive Cardiac Bypass Catheter Systems

Recent advances have been made in the field of "cardiac bypass procedures" which include the use of novel catheter assemblies which are adapted to temporarily arrest and bypass the heart without the need for direct cross-clamping or externally tying the vena cavae. Such assemblies are generally herein referred to by the terms "minimally invasive catheter bypass systems," or derivatives of these terms, and generally include an arterial catheter, which isolates the left heart chambers from systemic arterial circulation beyond the aortic root, and a venous catheter, which isolates the right heart chambers from venous circulation from the vena cavae. Further to the intended meaning, such minimally invasive catheter bypass systems may be used during procedures which otherwise still require a sternotomy in an otherwise "open chest" or "open heart" procedure which directly exposes the heart, as well as during procedures which otherwise alleviate the need for such sternotomies, such as for example procedures known as "port access" procedures.

One particular example of a previously known "minimally invasive cardiac bypass system" uses an arterial catheter which occludes the aorta from systemic arterial circulation with an inflatable balloon located on the outside surface of the catheter's distal end portion which is positioned within the aorta. The arterial catheter further includes a cannula with lumens and distal ports which provide for cardioplegia agent delivery and venting of the left ventricle, respectively, while the heart is isolated from systemic circulation with the inflated balloon on the outer surface of the arterial catheter. Further to this known system, a venous catheter is further provided and uses a balloon in each of the superior and inferior vena cava. The venous catheter balloons inflate to occlude these great veins and thereby isolate the right heart chambers from systemic venous blood flow. Moreover, the venous and arterial catheters which combine to form minimally invasive cardiac bypass catheter systems engage to inlet and outlet ports, respectively of a cardiopulmonary bypass pump, which pump may be further considered a part of the overall system. One such known pump which is believed to be particularly usefull in cardiac bypass procedures, including minimally invasive bypass procedures, is known as the "BioPump", Model Number "BP80", which is available from Medtronic, Inc.

Further to the description for the minimally invasive cardiac bypass system example just provided above, the terms "proximal" and "distal" are herein used throughout this disclosure as relative terms. In the context of describing a device or catheter used in such a system, the term "proximal," such as in the phrase "proximal end", is herein intended to mean toward or closer to a user such as a physician, whereas the term "distal," such as in the phrase "distal end" is herein intended to mean away from or further away from the user. However, if and where the terms "proximal" and "distal" are herein used in the context of describing anatomical structures of the cardiovascular system or physiological blood flow, the term "proximal" is herein intended to mean toward or closer to the heart, whereas the term "distal" is herein intended to mean away from or further from the heart. Furthermore, the terms "upstream" and "downstream" are also relative terms which may be herein used interchangeably with "proximal" or "distal", respectively, in the anatomical or physiological context just described.

According to the method of using known minimally invasive cardiac bypass catheter systems such as the example summarized above, the heart is usually put on "partial bypass" prior to "complete bypass". The terms "partial bypass" are herein intended to mean a condition wherein the heart is beating and pumping blood throughout the body's circulation prior to inflating the balloons on the arterial and venous catheters, and wherein some blood is also aspirated from the vena cavae through the venous catheter, sent through the cardiopulmonary bypass pump, and infused into the arterial circulation through the flow ports along the arterial catheter. The terms "complete bypass" or "full bypass" or derivatives thereof are therefore herein intended to mean a condition wherein the heart is substantially isolated from systemic venous and arterial circulation by means provided by the venous and arterial catheters, respectively, such as for example by inflating balloons on the exterior surfaces of such venous and arterial catheters to thereby totally occlude the vena cavae and aorta, also respectively, as described above.

According to these definitions for partial and full bypass just provided, a patient is therefore put on partial bypass by first positioning the venous and arterial catheters at respectively predetermined locations along the vena cavae and aorta, respectively, such that the respective flow ports may provide for the respective aspiration or infusion of blood and such that balloons on the catheter outer surfaces may be thereafter inflated to isolate the right and left heart chambers, also respectively, during fill bypass. The procedure for subsequently weaning a patient from partial bypass to full bypass according to the known minimally invasive cardiac bypass system example described above generally proceeds as follows.

Cardioplegia agent is delivered during partial bypass in order to begin reducing the cardiac function ultimately toward the temporarily arrested state. The external balloons are inflated to occlude the vena cavae and isolate the right heart from systemic venous circulation prior to inflating the arterial catheter's balloon to isolate the left heart from systemic arterial lo circulation. During this "weaning" period, the bypass pump circulates the blood aspirated from the vena cavae while the heart continues to pump a declining volume of residual blood from the coronary sinus, right heart chambers, pulmonary circulation (including lungs), and left heart chambers. As the residual volume of blood pumping through the heart declines, and as the cardiac function continues toward temporary arrest under cardioplegia effects, the balloon on the exterior surface of the arterial catheter is then inflated to occlude the aorta and finally achieve full or complete bypass.

Upon inflating the arterial balloon and totally occluding the aorta during the "weaning" period onto full bypass as just described, additional cardioplegia agent delivery continues distally of the inflated balloon. However, it has been observed that "back pressure" on the cardioplegia delivery cannula during cardioplegia agent delivery, together with the pressure from the beating heart against the totally occluded aorta, may push the arterial balloon downstream along the aorta. As a result, a user may be required to reposition the balloon at the initially desired location along the ascending aorta between the aortic root and the carotid arteries. It is believed that the repositioning of the arterial balloon in response to this pressure response may be performed while the balloon is inflated, or during subsequent iterations of positioning and then inflating in order to adjust for the observed post-inflation movement.

Still further to the known "minimally invasive cardiac bypass systems," weaning a patient off of "complete bypass" and off of the cardiopulmonary bypass pump while reestablishing physiological cardiac output generally requires deflation of the external balloon on the external surfaces of the arterial and venous catheters. However, some patients have been observed to present complications while cardiac function is being reestablished, which complications may require returning the patient back to a full bypass condition. Therefore, patients are generally kept in surgery for a prolonged period of time subsequent to deflating the balloons on the bypass system catheters and after reestablishing the cardiac function in order to observe the heart's recovery. In cases where such patients are required to be put back onto cardiac bypass, the balloons must be repositioned at their desired location and then reinflated to isolate the heart. Particularly regarding the occlusion balloon on the external surface of the arterial catheter, this reinflation while the heart is pumping may present the same repositioning issues as previously described above.

It is further believed that the arterial balloon repositioning which may be required during use of arterial catheters according to the known minimally invasive cardiac bypass systems may present a cumbersome and potentially dangerous detriment to the efficiency and safety of the overall minimally invasive cardiac bypass procedure.

There is a need for a minimally invasive cardiac bypass system which includes an arterial catheter with an external balloon which is adapted to inflate and engage the aortic wall to secure the catheter at a predetermined location along the ascending aorta between the aortic root and the carotid arteries along the aortic arch and which is further adapted such that the external balloon does not substantially reposition during such inflation while cardioplegia agent is being delivered to the heart through a cardioplegia cannula upstream from the external balloon or while the heart is beating such as when a patient is being weaned onto partial or full cardiac bypass.

There is also a need for a minimally invasive cardiac bypass system which includes an arterial catheter with an external balloon which is adapted to remain inflated and engaged to the aortic wall at a predetermined location along the ascending aorta while cardiac function is being reestablished as a patient is weaned off of a cardiopulmonary bypass pump subsequent to a surgical cardiac procedure.

There is also a need for a minimally invasive cardiac bypass system which includes an arterial catheter that is adapted to: anchor within the ascending aorta; shunt antegrade aortic blood flow from the aortic root, proximally through a flow lumen within the catheter past the anchor, and into the systemic arterial circulation downstream of the anchor while the heart is still beating during partial cardiac bypass; selectively occlude the shunted antegrade flow path, thereby isolating the aortic root from systemic circulation when the heart is temporarily arrested and on full cardiac bypass; and selectively provide a retrograde flow path through the internal flow lumen of the catheter for active infusion of oxygenated blood from a bypass pump and into the systemic arterial circulation proximally of the anchor when the heart is temporarily arrested during full cardiac bypass.

There is also a need for a minimally invasive cardiac bypass system which includes an arterial catheter which is adapted to shunt antegrade aortic blood flow before or during partial cardiac bypass from the aortic root, through a distal flow port into an internal flow lumen within the catheter, and out of the internal flow lumen through an intermediate flow port into systemic arterial circulation while minimizing hemolysis at the transition region between the aortic root and the distal flow port into the internal flow lumen and also while minimizing the movement of the arterial catheter.

There is also a need for a minimally invasive cardiopulmonary bypass system which includes a venous catheter which is adapted to substantially aspirate the venous blood from the vena cavae while substantially isolating the right ventricle from the vena caval blood flow without circumferentially engaging the interior wall of the inferior or superior vena cavae and without completely occluding the vena cavae.

SUMMARY OF THE INVENTION

The present invention is a minimally invasive bypass system which includes an arterial catheter and a venous catheter, each catheter being adapted to couple with a cardiopulmonary bypass pump in order to provide systemic circulation of oxygenated blood while the heart is isolated from the systemic circulation in a substantially bloodless field. The arterial catheter is adapted to wean a patient onto and off of cardiac bypass by using an external shunt valve in combination with internal valves within an internal flow lumen. The external and internal valves of the arterial catheter selectively allow for either: (1) antegrade perfusion of blood flow from a beating heart, proximally through the flow lumen, past an external shunt valve in a closed position within the aorta, out of ports located along the catheter proximally of the external shunt valve, and into the systemic arterial circulation; or (2) active perfusion of oxygenated blood from a cardiopulmonary bypass machine, distally through the flow lumen, and into systemic circulation also through ports located along the catheter proximally of the external shunt valve. The venous catheter is adapted to isolate the right ventricle from venous blood flow and to aspirate the venous blood from the vena cavae without circumferentially engaging the vena cavae with an expanded balloon.

One mode of the invention is a medical device assembly which is adapted for selectively shunting an antegrade flow of blood from an aortic root in an aorta of an animal and into a proximal region of the aorta which is located proximally of the aortic root. The assembly according to this mode includes an elongate body with a flow lumen which extends between a distal flow port, located on the body's distal end portion, and an intermediate flow port located along the elongate body proximally of the distal flow port.

In one aspect of this mode, an external shunt valve is located along distal end portion between the distal and intermediate flow ports. The external shunt valve includes an anchor and a funnel and is adjustable between an open position and a shunting position. In the open position the anchor and funnel are adapted to allow the antegrade blood flow to pass through an exterior space between the distal end portion of the elongate body and the aortic wall. In the shunting position the anchor is adapted to radially engage the aortic wall such that the distal end portion of the elongate body is secured at a predetermined location within the aorta. The funnel in the shunting position is adapted to substantially shunt the antegrade blood flow from the aortic root and into the flow lumen through the distal flow port while substantially isolating the exterior space around the catheter from that antegrade flow.

In one variation of this aspect, the external shunt valve is an expandable member that is adjustable from a radially collapsed condition to a radially expanded condition which forms the anchor and the funnel. The funnel includes a proximally reducing, tapered inner diameter from a large inner diameter portion to a reduced inner diameter portion which is located adjacent to the distal flow port. Further to this aspect, the expandable member may be an inflatable balloon which has an expanded shape that forms the anchor and the funnel.

In another aspect of this mode, a distal internal valve is coupled to the flow lumen between the distal and intermediate flow ports. In an open position, the distal internal valve is adapted to allow for fluid to flow through the flow lumen between the distal and intermediate flow ports. In a closed position, the distal internal valve is adapted to substantially isolate the distal flow port from the intermediate flow port through the flow lumen.

In one variation of this aspect, the distal internal valve is an expandable balloon which is adapted to selectively occlude the flow lumen when pressurized and adjusted to a radially expanded condition. The balloon may be located within the flow lumen, or may be located adjacent to a collapsible tubular member which forms at least a portion of the flow lumen. In the latter variation, expansion of the balloon collapses the collapsible tubular member to occlude flow therethrough.

In another variation of this aspect, the flow lumen further communicates externally of the elongate body through a proximal flow port located along the proximal end portion of the elongate body. A proximal internal valve is coupled to the flow lumen between the intermediate flow port and the proximal flow port and is also adjustable between open and closed positions. According to this variation, the distal internal valve may be adjusted to the open position with the proximal internal valve adjusted to the closed position such that antegrade blood flow from the aortic root may be shunted through the flow lumen between the distal and intermediate flow ports while the antegrade flow is isolated from the region of the flow lumen proximally of the proximal internal valve. By alternatively adjusting the distal internal valve to the closed position and the proximal internal valve to the open position, oxygenated blood from a cardiopulmonary bypass pump may be perfused distally through the flow lumen between the proximal and intermediate flow ports while the distal flow is isolated from the flow lumen distally of the intermediate flow port. Still further to this variation, an expandable balloon may be provided for the proximal internal valve.

In another variation of this aspect, an external shunt valve is provided along the distal end portion of the elongate body between the distal and intermediate flow ports and is adjustable between an open position and a closed position. The external shunt valve in the closed position forms an anchor to secure the valve at a predetermined location along the aorta and also forms a funnel which is adapted to selectively shunt antegrade flow of blood from the aortic root and into the internal flow lumen of the catheter through the distal flow port.

In still another variation of this aspect, a plurality of intermediate ports are provided along the elongate body proximally of the external shunt valve and between the distal and proximal flow ports. An intermediate internal valve is provided between each pair of adjacent intermediate ports and is adjustable from an open to a closed position. The distal, intermediate, and proximal internal valves are selectively adjustable to their respective open or closed positions such that a predetermined combination of intermediate ports may be perfused with blood either from the aorta, before isolating the heart from systemic circulation during bypass, or from the cardiopulmonary pump after isolating and stopping the heart during bypass.

Another mode of the invention is a medical device assembly which is adapted to selectively aspirate venous blood flow from the vena cavae while substantially isolating the right ventricle from the vena cavae and also Without circumferentially engaging the interior wall of the vena cavae. The assembly according to this mode includes an elongate body with a proximal end portion, a distal end portion, and a flow lumen which extends between a distal flow port located along the body's distal end portion and a proximal flow port located along the body's proximal end portion.

In another aspect of this mode, an external valve is located along the elongate body between the distal and proximal flow ports and is adjustable from an open position to a closed position. The external valve includes a valve member which is positioned at a discrete location around the body's circumference, which is adjustable from a first radial position to a second, radially displaced position adjacent to the elongate body, and which is further adjustable from a radially collapsed condition to a radially expanded condition when in the radially displaced position. The open position of the external valve is characterized by the first radial position of the valve member which is adapted to allow for the venous blood to flow from the vena cavae and into the right heart chambers. The closed position for the external valve is characterized by aligning the discrete circumferential location of the valve member with the sinus venarum between the vena cavae and the right atrium, thereafter adjusting the valve member to the radially displaced position which is located at least in part within the right atrium, and further adjusting the valve member to the radially expanded condition which is adapted to substantially isolate the right ventricle from the vena cavae. By adjusting the external valve to the closed position and coupling the proximal flow port to an inlet port of a cardiopulmonary bypass pump, blood within the vena cavae may aspirated into the distal flow port, along the internal flow lumen, and into the cardiopulmonary bypass pump.

In one variation of this aspect, the valve member includes two expandable members which are separated by a space. In the radially displaced position the valve member is adapted such that the two expandable members are positioned within the right atrium and right ventricle, respectively, wherein the valve that separates the right atrium and the right ventricle is positioned within the space. When the valve member is adjusted to the radially expanded condition the two expandable members expand to substantially narrow the space therebetween, thereby engaging the valve and isolating the right ventricle from the right atrium.

In another variation of this aspect, an intermediate flow port is located along the elongate body's distal end portion between the distal and proximal flow ports. The distal flow port is adapted to aspirate blood from the superior vena cava and the intermediate port is adapted to aspirate blood from the inferior vena cava. The distal and intermediate flow ports may communicate with a common venous flow lumen or with separate lumens, respectively.

In another aspect of this mode, an external valve is located along the distal end portion proximally of the distal flow port and is adjustable from a radially collapsed condition, which characterizes an open position, and a radially expanded condition, which characterizes a closed position. The external valve when in the closed position has an outer diameter which is slightly less than the inner diameter of the vena cava wall such that the external valve does not circumferentially engage the.vena cava and venous blood is only partially occluded through the vena cava. The external valve is thus adapted as a pressure cuff to increase the pressure in the region of the distal flow port to enhance the aspiration of that blood through that port, through the flow lumen, and into a cardiopulmonary bypass pump.

In one variation of this aspect, a distal flow lumen extends between the distal flow port and a first proximal flow port on the body's proximal end portion, and an intermediate flow lumen extends between an intermediate flow port, located along the distal end portion proximally of the external shunt valve, and a second proximal flow port also located along the body's proximal end portion. In a further variation, two external valves are provided—a distal external valve is located along the elongate body proximally adjacent to the distal flow port, and an intermediate external valve is located along the elongate body between the distal external valve and the intermediate flow port. The distal external valve is adapted for positioning within the superior vena cava between the distal flow port and the sinus venarum into the right atrium, while the intermediate external valve is adapted to be positioned within the inferior vena cava between the sinus venarum and the intermediate flow port. By adjusting the external valves to their respectively closed positions, venous blood flow is shunted from the vena cavae and into a cardiopulmonary bypass pump through the distal and intermediate flow lumens while the right heart chambers are substantially isolated from the venous flow. In still a further variation, a leakage port is also provided between the distal and intermediate external valves and may communicate proximally to an aspiration pump through its own lumen or through a shared lumen with either or both of the distal and intermediate flow ports.

Another mode of the invention is a method for isolating the left ventricle and aortic root of a mammalian heart from systemic arterial circulation during a cardiopulmonary bypass procedure. The method according to this mode includes positioning a distal end portion of an arterial catheter at a predetermined location within the aortic root; anchoring the distal end portion at the predetermined position; and shunting antegrade aortic blood flow from the aortic root to a proximal region of the aorta proximally of the predetermined position while isolating the antegrade aortic blood flow from an exterior space between the cannula and the aortic wall and also between the predetermined position and the proximal region.

One aspect of this method further includes shunting the antegrade aortic blood flow into an interior flow lumen which extends through the arterial catheter between a distal flow port located within the aortic root and an intermediate flow port located along the distal end portion of the elongate body proximally of the predetermined position.

One variation of this aspect includes adjusting an external shunt valve, which is located between the distal and intermediate flow ports, from a radially collapsed condition to a radially expanded condition that circumferentially engages the aortic wall and thereby substantially isolates the exterior space around the cannula from the antegrade aortic blood flow. This variation may further include funneling the antegrade blood flow from the aortic root and into the distal flow port of the flow lumen through a funnel formed by the external shunt valve.

Another variation of this aspect includes selectively preventing the antegrade aortic flow from passing through the flow lumen proximally of the intermediate flow port by selectively occluding the flow lumen between the intermediate flow port and a proximal flow port located along the proximal end portion of the catheter. This variation further includes adjusting a proximal internal valve located between the intermediate and proximal flow ports from an open position, which is adapted to substantially allow for flow through the flow lumen between the intermediate and proximal flow ports, to a closed position, which is adapted to substantially occlude flow between the intermediate and proximal flow ports.

Still a further variation of this aspect includes selectively preventing the antegrade aortic flow from passing through the flow lumen between the distal and intermediate flow ports adjusting an intermediate internal valve coupled to the flow lumen between the distal and intermediate flow ports to a closed position, thereby substantially occluding flow through the flow lumen between the distal and intermediate flow ports. This aspect further includes adjusting a proximal internal valve located between the intermediate and proximal flow ports to an open position, which is adapted to substantially allow for flow through the flow lumen between the intermediate and proximal flow ports. This aspect also further includes perfusing oxygenated blood through the intermediate flow port from a cardiopulmonary bypass pump which is coupled to the proximal flow port.

BRIEF DESCRIPTION OF THE DRAWINGS

FIGS. 3A–B show perspective views of another particular arterial catheter according to the present invention, wherein FIG. 3A shows a proximally oriented perspective view of the proximal end portion of the catheter and includes a perspective view of a transverse cross-section taken through the proximal end portion of the elongate body, and wherein FIG. 3B shows a distally oriented perspective view of the distal end portion of the catheter and includes a perspective view of a transverse cross-section taken through the distal end portion of the catheter's elongate body in the region of a proximal internal valve.

FIG. 3C shows a more detailed, perspective view of one particular means for constructing an internal valve according to the internal valve variation shown in FIG. 3B.

FIG. 4A shows a sectional perspective view of another particular arterial catheter according to the present invention, and includes a sectional perspective view of another particular internal valve design for use in selectively occluding an internal flow lumen through the catheter.

FIG. 4B shows a longitudinal cross-sectional view taken along line 4B—4B through the arterial catheter shown in FIG. 4A, wherein one particular distal internal valve is shown in a closed position and one particular proximal internal valve is shown in an open position.

FIG. 5A shows a longitudinal cross-sectional view of another arterial catheter according to the present invention, and further shows another particular internal valve assembly for use in selectively occluding an internal flow lumen through the catheter, and also shows one particular external shunt valve in a radially expanded condition which forms an anchor and a funnel for shunting antegrade aortic blood from an aortic root and into the internal flow lumen.

FIG. 5B shows a distally oriented transverse cross-sectional view taken through the elongate body of an arterial catheter similar to that shown in FIG. 5A.

FIG. 7A shows a perspective view of the distal end portion of another arterial catheter according to the present invention, and further shows one particular external shunt valve in a radially collapsed condition which characterizes an open position.

FIG. 7B shows a perspective view of the same distal end portion of the arterial catheter shown in FIG. 7A, although showing the external shunt valve in a radially expanded condition which characterizes a shunting position.

FIG. 7C shows a sectional longitudinal cross-section taken along line 7C—7C through the funnel formed by the external shunt valve shown in FIG. 7B.

DETAILED DESCRIPTION OF THE EMBODIMENTS

Figure 11:
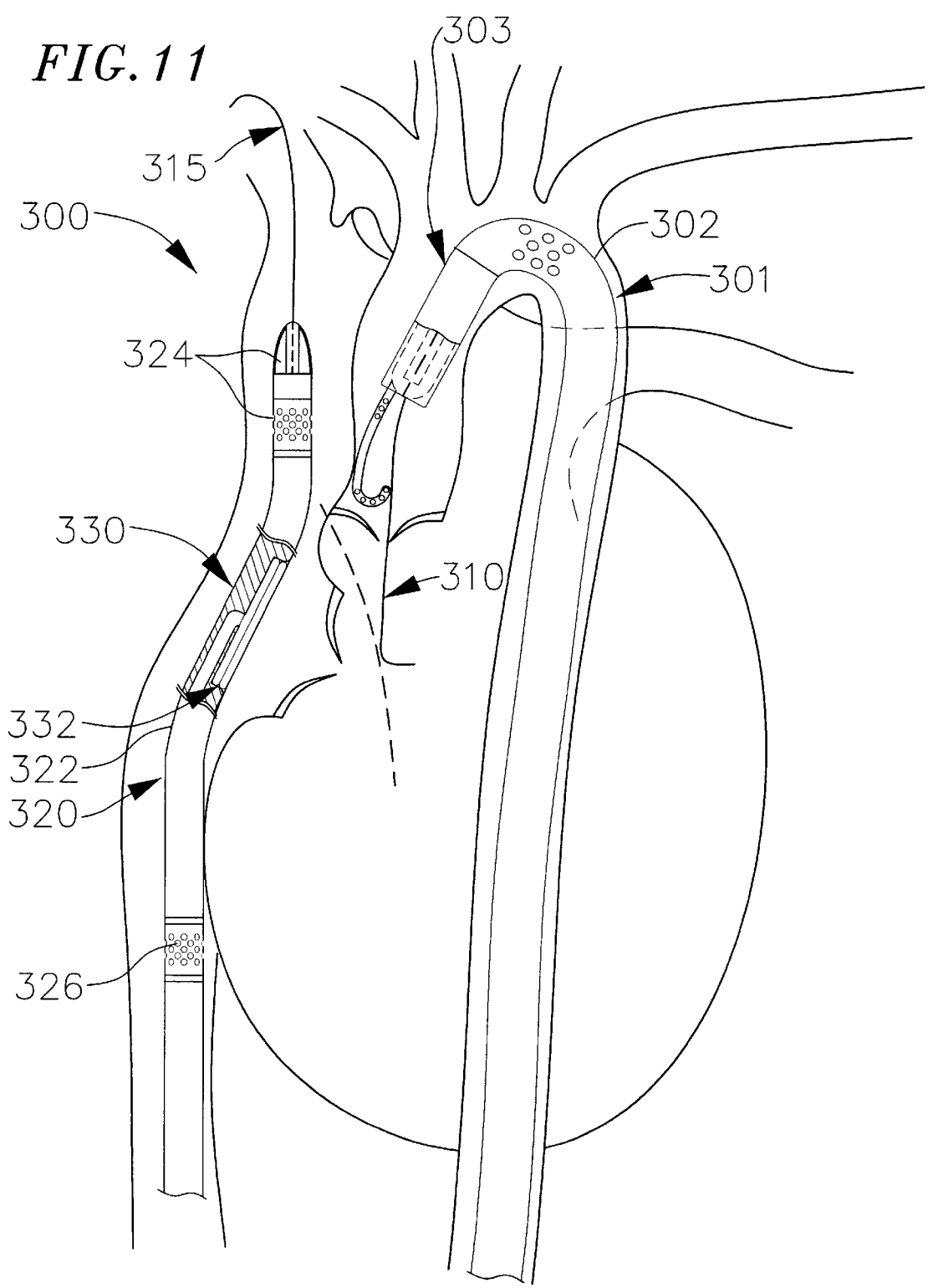
FIG. 11 shows a medical device assembly according to the present invention during use in performing a minimally invasive bypass procedure, and shows an arterial catheter with an external shunt valve in an open position during retrograde delivery through the ascending aorta and into the aortic arch, and also shows a venous catheter with an external valve in its open position during positioning within the vena cavae and prior to isolating the right heart chambers from venous blood flow.
Figure 12:
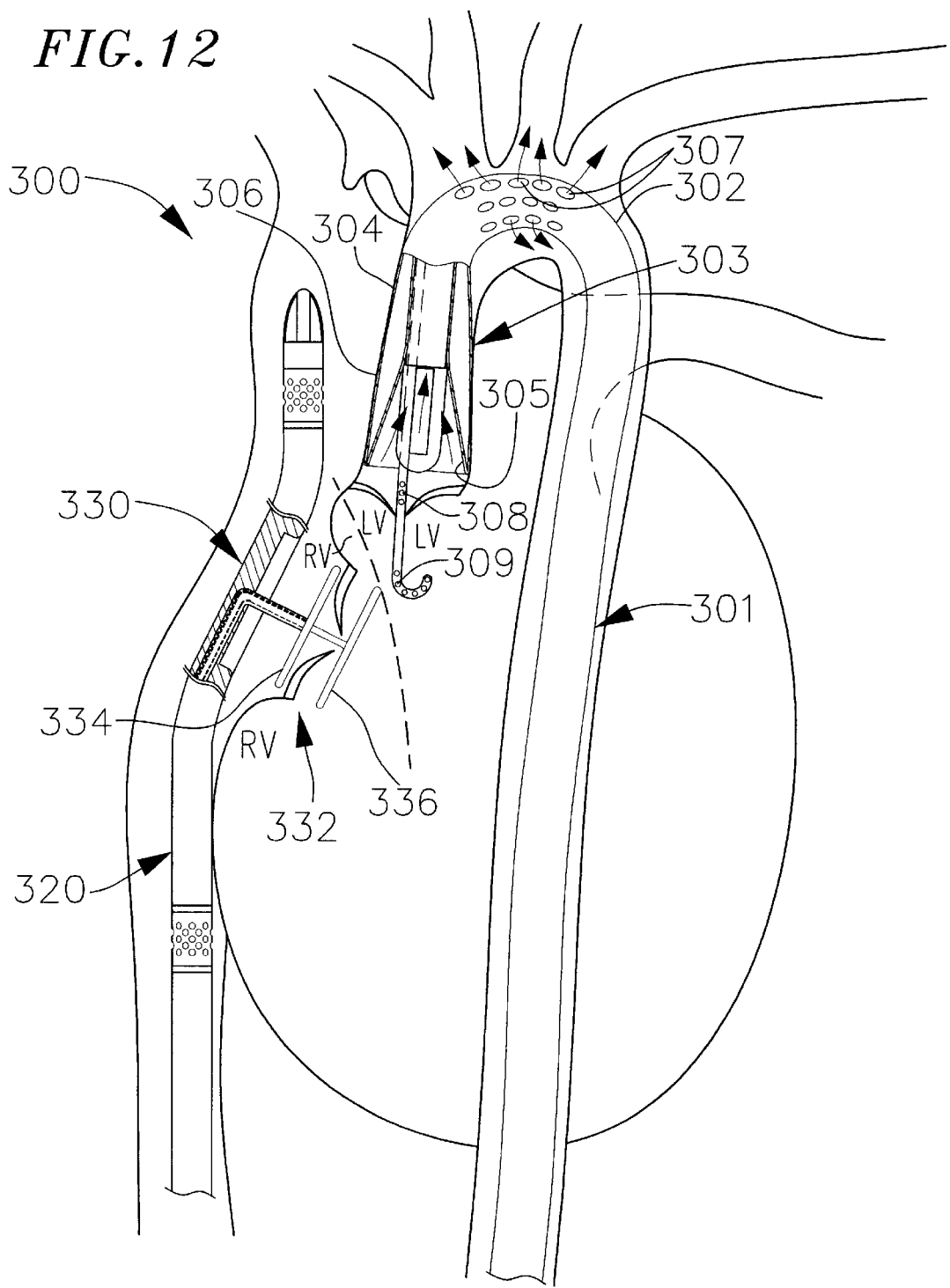
FIG. 12 shows a similar view of the medical device assembly shown in FIG. 11, although showing the external shunt valve of the arterial catheter in a radially expanded condition which characterizes a shunting position within the aortic arch, and also showing a valve member of the venous catheter's external valve after being adjusted to a radially displaced position which is adjacent to the elongate body and at least in part within the right atrium, and which positions the tricuspid valve within a space between two expandable members which form at least in part the valve member.
Figure 13:
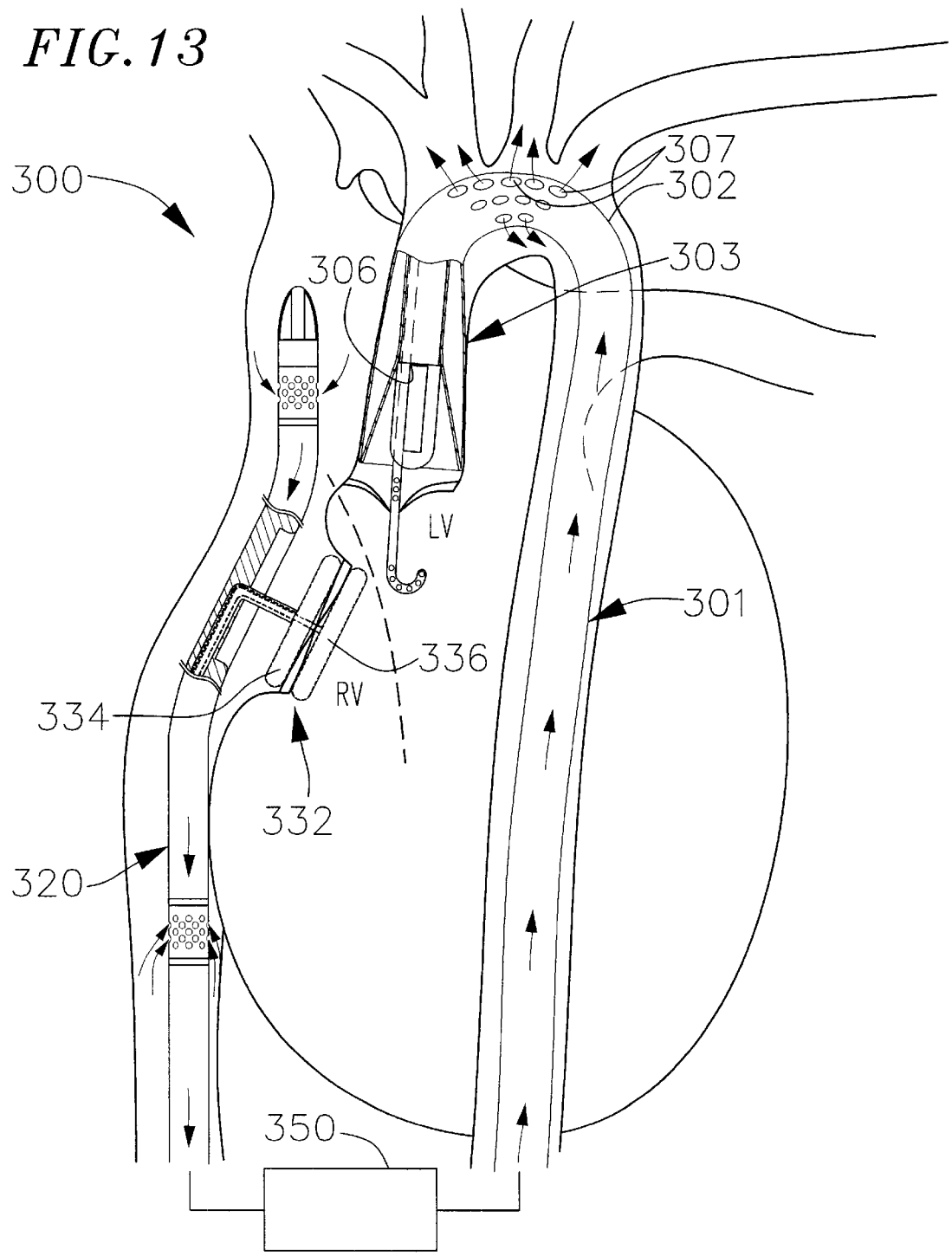
FIG. 13 shows a similar view of the medical device assembly as shown in FIGS. 11–12, although showing the two expandable members of the venous catheter's external valve after being adjusted to a radially expanded condition which thereby engages the tricuspid valve therebetween and isolates the right ventricle from the right atrium and the vena cavae, and also further showing arrows which represent venous blood as it is aspirated through distal and proximal flow ports positioned within the superior and inferior vena cavae, respectively.

FIGS. 1A–8D show varied detail of particular arterial catheter variations which are adapted for use in a minimally invasive cardiac bypass system according to the present invention. FIGS. 9–10D show varied detail of particular venous catheter variations which are also adapted for use in a minimally invasive cardiac bypass system according to the present invention. FIGS. 11–13 show a minimally invasive bypass catheter system according to the present invention during sequential modes of use in a cardiac bypass procedure.

Arterial Catheter

In general, the arterial catheter of the present invention is adapted such that its distal end portion may be positioned within the aortic root adjacent to the left ventricle while its proximal end portion is coupled outside of the body to a cardiopulmonary bypass pump. An external shunt valve anchors to the aortic wall along the ascending aorta between the aortic root and the aortic arch and allows for antegrade aortic blood flow to shunt from the aortic root, through an internal flow lumen within the catheter, and out an intermediate flow port located along the catheter proximally of the external shunt valve, usually in the region of the aortic arch.

Either during the cardiac output decline due to cardioplegic effects, or once the heart is substantially arrested from beating and is substantially drained of blood, an distal internal valve closes the internal flow lumen between the distal port adjacent the aortic root and the intermediate flow port in the region of the aortic arch, thereby isolating the left heart chambers from systemic arterial circulation. With the internal valve closed, oxygenated blood may then be perfused from the proximally coupled bypass pump, distally through the internal flow lumen, and out the intermediate flow port into the systemic circulation.

Figure 1A:
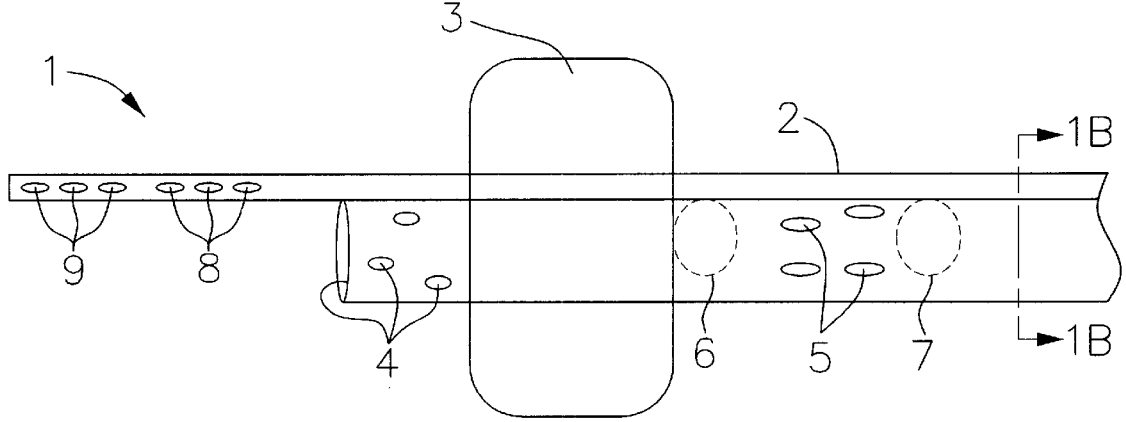
FIG. 1A is a schematic view of one arterial catheter of the present invention, showing in shadow two internal valves in closed positions within an internal flow lumen that extends within the catheter between distal and intermediate flow ports, and also showing an external shunt valve located between the distal and intermediate flow ports and in a radially expanded condition which characterizes a closed position.

FIG. 1A shows a schematic representation of the salient functional elements of the arterial catheter just described. Arterial catheter (1) is shown to include an elongate body (2) which includes an external shunt valve (3) on the outer surface of the elongate body's distal end portion. Elongate body (2) further includes an internal flow lumen (not shown in FIG. 1A) which communicates externally of the elongate body through a distal flow port (4), which is located distally of external shunt valve (3), and also through an intermediate flow port (5), which is located along the distal end portion of the elongate body proximally of external shunt valve (3). Each of the particular distal and intermediate flow ports (4,5) shown in FIG. 1A includes a plurality of apertures which are adapted to allow for sufficient wall rigidity for the catheter to function in a percutaneous transluminal procedure and also to allow for sufficient blood flow to communicate with the internal flow lumen through those ports.

FIG. 1A further shows a distal internal valve (6), which is located within the internal flow lumen distally of intermediate flow port (5), and also a proximal internal valve (7), which is located within the internal flow lumen proximally of intermediate flow port (5). Each of the distal and proximal internal valves (6,7) is adjustable from an open position, which allows for fluid flow to pass through the internal flow lumen, to a closed position, which is adapted to substantially occlude the internal flow lumen and prevent fluid flow from passing therethrough. Both distal and proximal internal valves (6,7) are shown in their respectively closed positions in FIG. 1A for the purpose of illustrating their location in relation to intermediate flow port (5).

A predetermined combination of the open and closed positions for the respective distal and proximal internal valves (6,7) shown in FIG. 1A may be selected such that a predetermined flow pattern is provided from the internal flow lumen and through these ports. For example, the distal internal valve (6) may be adjusted to the open position while the proximal internal valve (7) is adjusted to the closed position. In that arrangement, expansion of the external shunt valve (3) within an aortic arch in the region of the aortic root isolates an exterior space between the catheter and the aortic wall from antegrade aortic blood flow while that flow is shunted into distal flow port (4), through the internal flow lumen, out intermediate flow port (5), and into a proximal region of the aorta located proximally of the external shunt valve (3). Alternatively, distal internal valve (6) may be adjusted to the closed position while proximal internal valve (7) is adjusted to the open position. In this arrangement, intermediate flow port (5) may be fluidly coupled to a cardiopulmonary bypass pump via a proximal flow port (not shown) through which the internal flow lumen communicates exteriorly of the elongate body (2) along its proximal end portion (not shown).

Further shown in FIG. 1A are cardioplegia delivery port (8) and ventricular venting port (9), which are each shown to include a plurality of apertures. These ports (8,9) are shown located on a single, common cannula member which extends from the elongate body (2) distally of the distal flow port (4) and external shunt valve (3). It is further contemplated however that these delivery ports may also be on separate cannula members, and in either case the common or separate cannula member may be fixed relative to the elongate body (2) or may be individually slideable relative to elongate body (2), such as by being coaxially disposed within a lumen extending through the elongate body.

Regardless of the particular cannula design, however, the cardioplegia delivery port (8) is adapted to be positioned within the aortic root such that cardioplegia agent may be delivered to the heart via the coronary arteries stemming therefrom. As such, cardioplegia delivery port (8) may also be positioned adjacent to the distal flow port (4), so long as cardioplegia delivery port (8) is located distally of external shunt valve (3) in order to locally delivery the cardioplegia agent to the left heart and isolate the cardioplegia agent delivered from systemic circulation. The ventricular venting port (9) is adapted to be positioned within the left ventricle, ideally within the apex of that chamber, when the external shunt valve (3) is positioned and anchored within the aortic arch. In this manner the ventricular venting port (9) is adapted to aspirate blood from the left ventricle to create a substantially bloodless field during cardiac surgery when the heart is on bypass.

Figure 1B:
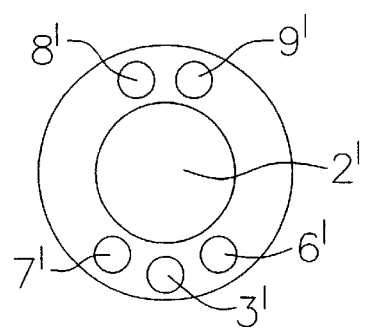
FIG. 1B is a cross sectional view taken along line 1B—1B of FIG. 1A and schematically shows the lumens of the arterial catheter.

FIG. 1B schematically shows the luminal structure of the apparatus of FIG. 1A. Interior flow lumen (2') extends throughout the catheters length between the distal flow port (4) shown in FIG. 1A and a proximal flow port located on the proximal end portion of the elongate body (not shown), and further communicates exteriorly of the elongate body (2) through intermediate flow port (5) shown in FIG. 1A. It is further contemplated that more than one lumen may function as internal flow lumens according to the present invention, so long as the distal and intermediate flow ports may be selectively fluidly coupled and the intermediate and proximal flow ports may also be selectively fluidly coupled. In one variation not shown, a distal internal flow lumen may extend between distal and intermediate flow ports, respectively, while a proximal internal flow lumen extends between proximal and intermediate flow ports, also respectively. According to this variation, separate intermediate flow ports may be provided in communication with the distal and proximal internal flow lumens, respectively, with the distal and proximal internal valves also positioned within the distal and proximal internal flow lumens, also respectively.

FIG. 1B further shows a schematic representation for external shunt valve actuating lumen (3'), distal internal valve actuating lumen (6'), proximal internal valve actuating lumen (7'), cadioplegia delivery lumen (8'), and left ventricular venting lumen (9'). These lumens are respectively coupled to external shunt valve (3), distal and proximal internal valves (6,7), and cardioplegia and left ventricular venting ports (shown in FIG. 1A). Furthermore, these lumens extend along the proximal end portion of the elongate body (not shown) and are respectively adapted to couple to an external shunt valve actuator, a distal internal valve actuator, a proximal internal valve actuator, a pressurizeable cardioplegia agent source, and a decompression pump. Moreover, the present invention should not be limited to the specific luminal structures and proximal actuation means described herein in detail and modifications and improvements thereof may be suitable according to one of ordinary skill.

Figure 2A:
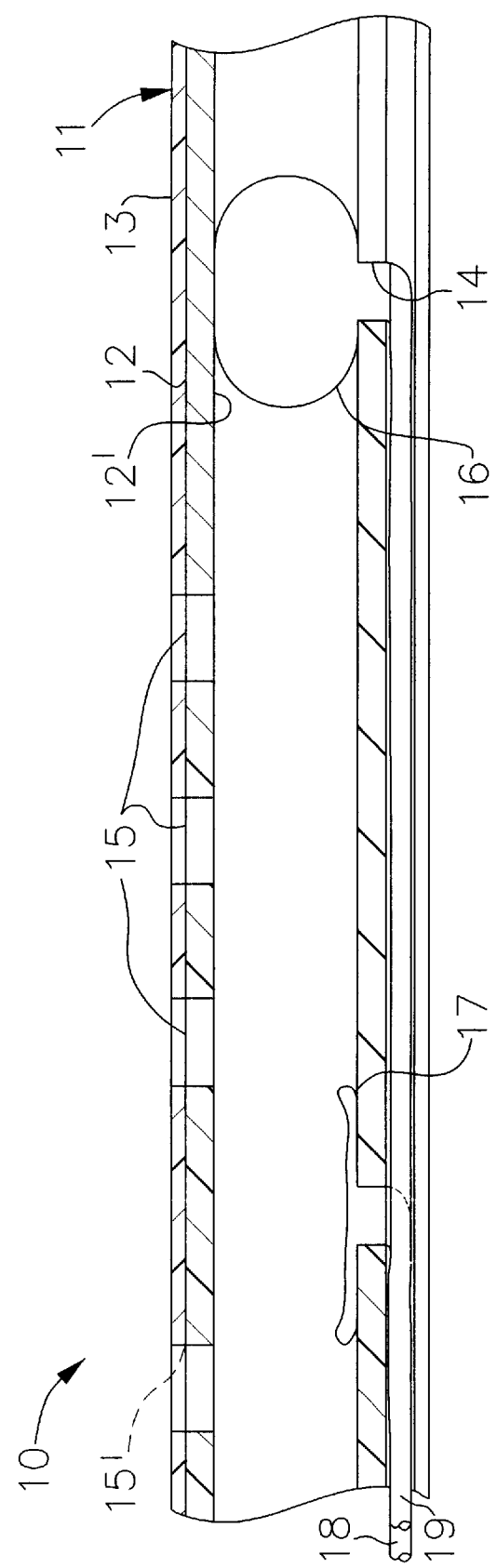
FIG. 2A shows a longitudinal cross-sectional view of one particular arterial catheter according to the schematically shown design of FIGS. 1A–B, and shows one particular internal valve structure which uses a balloon within the internal flow lumen for use in selectively occluding the internal flow lumen.

FIG. 2A shows an arterial catheter variation according to the present invention and which includes one particular internal valve variation that uses an expandable member to selectively occlude flow through an internal flow lumen within the catheter. Arterial catheter (10) is shown in FIG. 2A to include an elongate body (11) which includes an inner tube (12) that forms the internal flow lumen (12'). Distal internal valve (16) and proximal internal valve (17) are expandable members, specifically shown in FIG. 2A as expandable balloons, which are positioned distally and proximally adjacent to intermediate flow port (15), respectively, within internal flow lumen (12'). Intermediate flow port (15) further includes a plurality of apertures through inner tube (12) and through which the internal flow lumen (12') communicates exteriorly of elongate body (11). Each of distal and proximal internal valves (16,17) is adjustable from a radially collapsed position, which characterizes an open position that allows for fluid to flow through the internal flow lumen, to a radially expanded condition which characterizes the closed position, which is adapted to substantially occlude fluid flow through the internal flow lumen. For the purpose of further illustration, proximal internal valve (17) is shown in the radially collapsed condition, which is the open position, and distal internal valve (16) is shown in the radially expanded condition, which is the closed position.

FIG. 2A further shows a shadowed view of an additional flow port which is a second intermediate flow port (15') positioned proximally of proximal internal valve (17). Where multiple intermediate flow ports are provided according to this variation, a proximal internal valve is positioned proximally of the most proximally positioned intermediate flow port, and an intermediate internal valve is positioned along the internal flow lumen between each adjacent pair of intermediate flow ports. Thus, when second intermediate flow port (15') is included in the catheter shown in FIG. 2A, proximal internal valve (17) would actually be an "intermediate internal valve" and another proximal internal valve (not shown) would be provided along the internal flow lumen proximally adjacent to the second intermediate flow port (15').

Further to the multiple intermediate flow port variation just described, the distal, intermediate, and proximal internal valves may be adjusted to a predetermined combination of their respectively open and closed positions in order to provide fluid communication between either the proximal flow port or the distal flow port and a desired combination of the intermediate flow ports along the elongate body's length. For example, in the case where two intermediate flow ports (15,15') are provided such as according to FIG. 2A, antegrade aortic blood flow may be shunted proximally through internal flow lumen (12') from the distal flow port (not shown in FIG. 2A) and through only intermediate flow port (15) by adjusting internal valves (16,17) to their open and closed positions, respectively. Alternatively, by opening both internal valves (16,17) and closing a proximal internal valve (not shown) located proximally of second intermediate flow port (15'), the antegrade aortic blood flow may be shunted from the aortic root and to proximal regions of the aorta adjacent to both intermediate flow ports (15,15'). A different combination of internal valves may be adjusted to their respective open and closed positions in order to allow for the preselected distal perfusion of oxygenated blood from a bypass pump coupled to a proximal flow port (not shown) and through only intermediate flow ports (15') or both intermediate flow ports (15',15).

The controllable perfusion of oxygenated blood along the arterial catheter's length as just described is believed to address a dichotomy of functional requirements normally placed upon a minimally invasive bypass arterial catheter. In one aspect, the arterial catheter must be have a large enough internal flow lumen to carry oxygenated blood from the bypass pump or from the aortic root and into the aortic arch at flow levels which mimic physiological circulation. In another aspect, however, the arterial catheter itself provides occlusive resistance to antegrade arterial flow around the catheter between the intermediate flow ports located within the aortic arch and the catheter's entrance site, usually at the femoral artery. With the ability to perfuse blood flow through a predetermined length of ports along the arterial catheter, much of the desired downstream blood flow may be perfused out from the catheter further down the arterial tree and thus minimize the otherwise occlusive nature of the catheter shaft.

However, the controllable perfusion along the catheter's length according to the multiple valve and port embodiment shown in FIG. 2A has limited controllability. For example, a distal flow port may communicate with a controllable length of ports going distal to proximal along the catheter, but may not communicate with a selected port or ports on a proximal end portion of the catheter at the exclusion of more distal or intermediate ports. A similar limitation is present for the proximal flow port which is adapted to couple to an outlet port of a cardiopulmonary bypass pump. By selecting a specific internal valve to close, the proximal flow port communicates with any number of intermediate flow ports along the catheter proximally of the closed valve, but is isolated from intermediate flow ports located distally of the internal flow lumen. However, it may be desirable to select only one or a few distally disposed intermediate ports for active perfusion from the pump, such as for example an intermediate flow port located proximally adjacent to the external shunt valve which is adapted to be positioned adjacent to the ostia of the carotid arteries from the aortic arch.

The present invention therefore further contemplates use of a slideable external sheath positioned externally of the catheter shaft and which is adjustable to coaxially block and occlude selected intermediate flow ports along the catheter length. When a patient is on full or partial bypass, the slideable sheath may be positioned to a desired location distally along the catheter shaft such that a predetermined length of distally disposed intermediate flow ports is in communication with the proximal flow port, which predetermined length includes an intermediate port proximally adjacent to the external shunt valve but excludes any intermediate ports located more proximally along the catheter shaft.

Figure 3A:
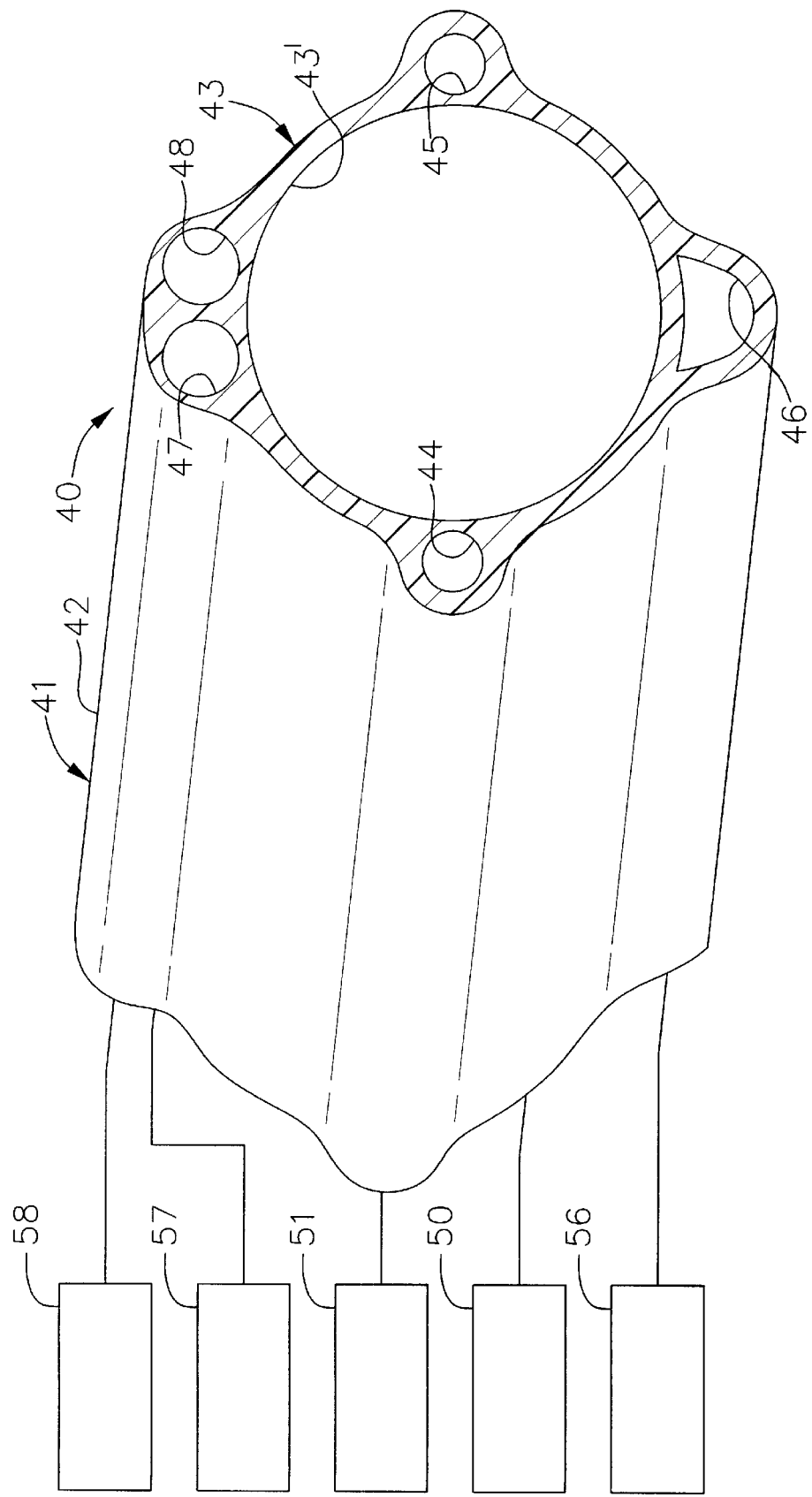

Further to the internal valve variation of FIG. 2A, distal and proximal internal valves (16,17) are expandable balloons which are shown to be fluidly coupled to distal and proximal valve actuating lumens (18,19), respectively, through ports formed through the wall of inner tube (12), shown for example in FIG. 2A at internal valve port (14). Various means for coupling the internal valves to their respective actuating members or lumens may be suitable according to one or ordinary skill. One particular means for providing such coupling is shown in FIG. 3C (described in detail below), which is particularly adapted for use in the elongate body variation shown in FIGS. 3A–B, but which may be suitably modified for use in the variation shown and described here by reference to FIG. 2A.

In order to actuate expansion of the balloons which form the internal valves of the FIG. 2A variation, distal and proximal valve actuating lumens (18,19) are also fluidly coupled to an internal valve actuator at the proximal end portion of the elongate body (not shown). The internal valve actuator may include one common actuator which includes a switch to selectively adjust each valve to its respective open or closed position, or may include separate, individual proximal and distal valve actuators, each coupled to one of the internal valves to adjust it between the respective valving positions. In either the common actuator or individual actuator case, the internal valve actuator generally includes a pressurizeable source of fluid for the balloon internal valve variation shown in FIG. 2A.

The expandable balloons used for internal valves (16,17) shown in FIG. 2A may be constructed as follows. In one variation, the balloon is constructed from a relatively compliant material which stretches when pressurized, such as for example a latex rubber, polyurethane, or silicone material. In this compliant balloon variation, the balloon may form a simple tubular member or otherwise a relatively small bladder when in the radially collapsed condition which characterizes the open position for the valve. Preferable to the small bladder variation and when placed within the internal flow lumen, the balloon is generally maintained under negative vacuum pressure when in the open position so as to minimize the occlusive nature of the balloon within the flow lumen. Upon pressurizing the relatively compliant balloon, the balloon material stretches and expands to form a balloon-like shape in the radially expanded condition which characterizes the closed position and blocks the internal flow lumen.

In another internal valve variation, the balloon is constructed from a relatively non-compliant material which is pre-formed into its desired shape in the radially expanded condition and is then subsequently folded into the radially collapsed condition which characterizes the open position for the valve. Such a relatively non-compliant balloon may be comprised of for example a radiated polyethylene material such as linear low or high density polyethylene, polyester terepthalate (PET), polyimide, Nylon, or polyolefin copolymer. Upon pressurization the folded, relatively non-compliant balloon is filled and unfolds to its radially expanded condition which characterizes the closed position and blocks the internal flow lumen.

While the particular internal valve variation shown in FIG. 2A places expandable balloons within the internal flow lumen (12'), other internal valve variations may also be suitable so long as the valve is adjustable from an open position, which allows fluid to flow through the internal flow lumen, to a closed position, which substantially occludes the internal flow lumen and blocks flow therethrough. For example, expandable members such as the balloons shown in FIG. 2A may be positioned adjacent to an inner tube which forms the internal flow lumen, rather than within the flow lumen. According to this variation, expansion of the expandable valve member to the radially expanded condition collapses the adjacent inner tube to create the closed position. By adjusting the expandable valve member to the radially collapsed condition, the inner tube distends to the open position for flow. This variation beneficially removes the expandable member of the internal valve from the flow lumen, which is believed to provide improved hemodynamics through a smoother surface within that lumen.

Further to the "adjacent" expandable valve member variation, the inner tube may be in one aspect a relatively thin-walled, flaccid member such as a thin polyethylene or a Teflon™ tubing such as those used in forming artificial graft members. The thin, flaccid inner tubing which forms the internal flow lumen according to this particular variation may be provided as follows. The thin, flaccid inner tubing which forms the internal flow lumen is a first inner tubing which has a diameter that approximates the inner diameter of a second inner tubing. The expandable balloon resides between the first and second inner tubings which are coaxial. With the internal valve in the radially collapsed condition which characterizes the open position, the first inner tubing distends from pressure within the internal flow lumen and fills the inner confines of the second, coaxial inner tubing. This pressure is provided for example by blood flowing either from the aorta and between the distal and intermediate flow ports or from the cardiopulmonary bypass pump and between the proximal and intermediate flow ports. However, when the internal valve is adjusted to the radially expanded condition which characterizes the closed position, the region of the first inner tubing adjacent to the internal valve is collapsed and the flow lumen is closed.

In a further variation (not shown) of the "adjacent" expandable valve member, the inner tube is a resilient tubular member, such as for example a polyurethane or silicone tubing. According to this variation, the resilient tubing elastically returns to the tubular state upon adjusting the valve to the open position after collapsing the tubing with the valve in the closed position.

In still another expandable internal valve member embodiment (not shown), a mechanically expandable member may be employed to selectively open and close the lumen, as opposed to the hydraulic actuation mechanism of the previously described balloon variations. In one such mechanical valve variation, an expandable cage constructed of coiled or braided metal ribbon or wires may be substituted for the inflatable balloons. In a more detailed embodiment where the cage is positioned within the flow lumen, such a cage would preferably include a distensible polymeric skin in a composite construction in order to substantially occlude flow therethrough during the expanded, closed position. In an alternative embodiment which places the expandable cage member adjacent to the internal flow lumen, however, such a composite skin might not be required.

In another further mechanical valve variation (also not shown), a stop-cock may be placed along the internal flow lumen. The open position for the stopcock variation is characterized a stopcock lumen being registered and aligned with the internal flow lumnen. The stopcock's closed position is characterized by the stopcock lumen being out of alignment from the internal flow lumen such that a wall of the stopcock blocks flow through the flow lumen. Adjustment of the stopcock between the open and closed positions may be accomplished mechanically, such as for example by keying a longitudinally adjustable actuating member to a curyed surface of the stopcock in a ratchet-and-pawl mechanism to rotate the stopcock.

Still a further mechanical internal valve variation (also not shown) includes a cam assembly with a cam surface that biases a longitudinally adjustable member radially into the internal flow lumen or against an inner tubing to collapse the flow lumen when the longitudinally adjustable member is advanced against the cam surface.

In addition to the several internal valve variations just previously described, other further variations not herein specifically described may also be suitable for use according to the present invention, as would be apparent to one of ordinary skill from this disclosure.

Further to the shaft construction shown in the arterial catheter embodiment of FIG. 2A, outer tubing (13) is shown surrounding inner tubing (12) as well as the internal valve actuating lumens (18,19) to form elongate body (11). Alternative variations of acceptable luminal structures for use in forming the elongate body of the FIG. 2A arterial catheter variation are provided in detail in FIGS. 2B–C, each showing a proximal end view through a cross section taken through a catheter's elongate body similar to that shown in FIG. 2A, and each showing an end perspective view of internal valves (16,17) in their closed and open positions, respectively, within the internal flow lumen.

Figure 2C:
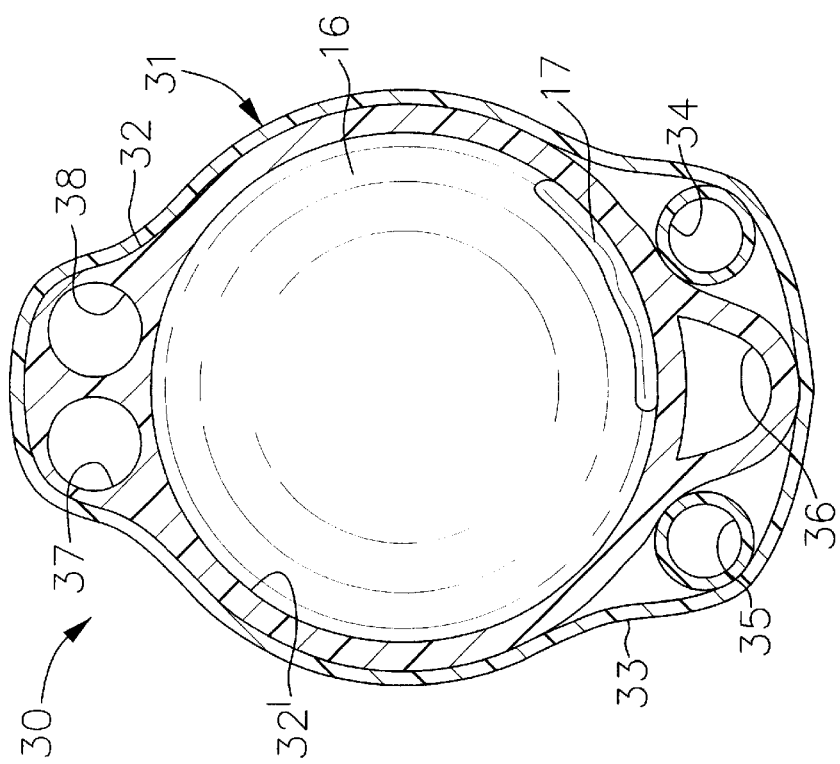
FIG. 2C is a similar transverse cross-sectional view as that shown in FIG. 2B, although showing another particular luminal construction for a catheter such as that shown in FIG. 2A.
Figure 2B:
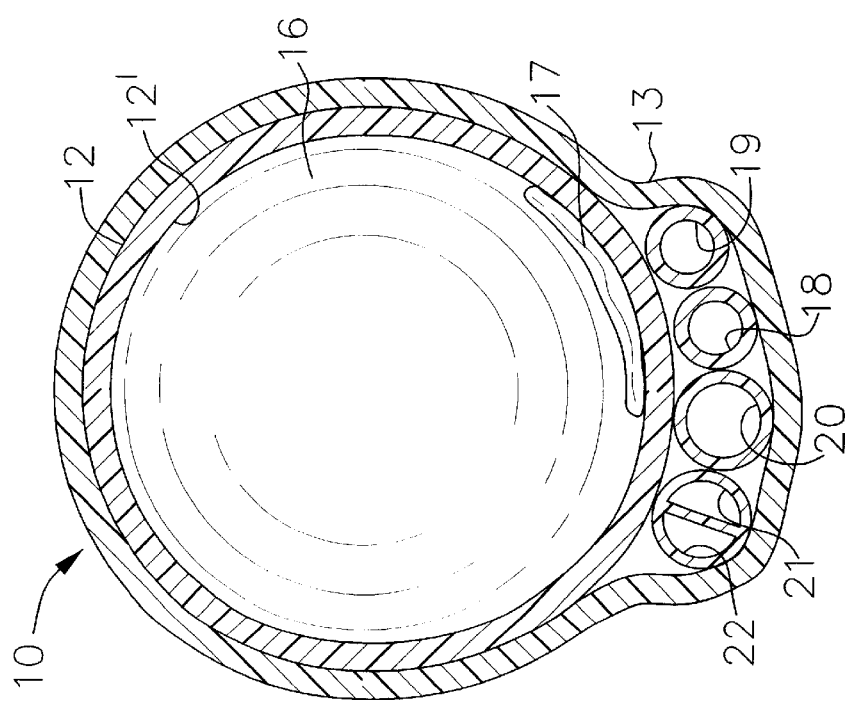
FIG. 2B is a distally oriented perspective view taken through a transverse cross-section of an elongate body in an arterial catheter similar to that shown in FIG. 2A.

One specific catheter shaft construction wherein each individual lumen is formed by a separate, individual tubing is shown in FIG. 2B. According to the FIG. 2B shaft variation, a bundle of inner tubings is coaxially surrounded and bound by an outer tubing (13) to form one, overall composite structure. Included within the bundle formed by outer tubing (13) are inner tubing (12), internal valve actuating lumens (18,19), external shunt valve actuating lumen (20), and cardioplegia delivery and ventricular venting lumens (21,22).

Unlike the other lumens shown in FIG. 2B, cardioplegia delivery and ventricular venting lumens (21,22) are shown in FIG. 2B to be formed by a dual lumen extrusion. This particular design is believed to be particularly usefull in the bundled composite shaft variation because these particular lumens are preferably extended distally beyond the structures along the elongate body's distal end portion to which the other lumens couple and terminate. For example, the internal valve actuating lumens (18,19) terminate distally in the internal valves, such as at valves (16,17) shown in FIG. 2A or at valves (6,7) shown in FIG. 1A. Furthermore, external shunt valve actuating lumen (20) terminates distally where it is fluidly coupled to the external shunt valve, such as is shown at external shunt valve (3) in FIG. 1A. Still further, the internal flow lumen formed by inner tubing (12) terminates distally at a distal flow port such as distal flow port (4) shown in FIG. 1A.

Another acceptable luminal variation for use in forming the elongate body of an arterial catheter according to the variation shown in FIG. 2A is shown in FIG. 2C. In this variation, a single, four lumen extrusion (32) forms internal flow lumen (32'), an external shunt valve actuating lumen (36), and cardioplegia delivery and ventricular venting lumens (37,38). Separate, individual internal valve actuating lumens (34,35) are also shown bundled together with four lumen extrusion (32) within an outer tubing (33) to form the composite shaft of this variation.

The positioning of the separate lumens in the four lumen extrusion (32) of FIG. 2C enhances the ability for those separate lumens to be cut away from the rest of the extrusion where an adaption is to be desirably formed. For example, the portion of four lumen extrusion (32) which forms external shunt valve actuating lumen (36) may be removed distally to where external shunt valve actuating lumen (36) is to be fluidly coupled and adapted to the external shunt valve (not shown), thereby extending a three lumen extrusion containing internal flow lumen (32'), cardioplegia delivery lumen (37), and ventricular venting lumen (38) distally from that adaption. Similarly, the three lumen extension of four lumen extrusion (32) may be further modified distally of the external shunt valve adaption, such that a two lumen extension which forms cardioplegia delivery and ventricular venting lumens (37,38) may be carried distally of the cut-away portion forming the internal flow lumen (32'). However, in a further variation to the latter example (not shown), the three lumen extension of the four lumen extrusion (32) may alternatively terminate at one location, wherein cardioplegia delivery and ventricular venting lumens (37,38) may be adapted to a separate dual lumen cannula (or two separate tubings) which carry the lumens further distally where they terminate in their respective distal ports (not shown).

One suitable assembly method and material construction for the individual tubings used in the bundled composite shaft variations just shown and described by reference to FIGS. 2B–C may be provided as follows. The outer tubing, such as outer tubing (13) in FIG. 2B or outer tubing (33) in FIG. 2C, is preferably a heat shrinkable polymer which may be comprised of for example irradiated polyethylene, polytetrafluoroethylene (PTFE), fluoro ethyl propylene (FEP), polyester terepthalate (PET), or polyimide. In general, such a heat shrinkable polymer is heated and then expanded from a memory state to an expanded state. In the expanded state, the heat shrink tubing is loaded coaxially over the other inner tubings. During subsequent reheating, the outer, expanded, heat shrink tubing recovers toward the smaller diameter memory state and thus shrinks around the inner tubings to form the composite.

The inner tubings according to the bundled construction just described are preferably adapted to resist deformation and also to retain their luminal integrity under the elevated temperatures of the heat shrink process just described. To that end, placement of mandrels through the bundled tubings is one method which is believed to assist in maintaining these interior lumens during the heat shrink process. In the alternative or in addition to providing mandrels within the respective lumens, one or all of the inner tubings may also be made of an irradiated polymer, which may be similar to that used for the outer heat shrink tubing, although such inner radiated tubings are preferably at their memory state and are, collapsed such that they maintain their lumens during the heat shrink step. In a further variation, the inner tubings may be made of a material with a melt temperature or glass transition temperature which is higher than the temperature required to shrink the outer tubing. In still a further variation, one or all of the inner tubings may include a reinforcing member such as a metallic coil or braid imbedded within or laminated with a polymeric tube which assists in maintaining the tubular shape when the polymer might otherwise flow and reconfigure when the bundle is heated with the outer tubing.

Further to the heat shrink-bundling variations just described, one or more additional polymeric members may also be provided between or around the individual inner tubings as they are bundled and heated to form the composite. Such additional polymeric members preferably are comprised of a material which melts and flows at the temperatures used to shrink the outer heat shrink tubing. For example, non-irradiated low density polyethylene tubings or beading mandrels may be included around or between the inner tubings, respectively. When the bundle is heated during the heat shrink-bundling process, this additional polymeric tubing or mandrel melts and flows between the inner and outer tubings and provides a binding agent therebetween. Further to this variation, a flexible epoxy or other adhesive material may also be provided between the interior tubings as a binding agent during the heat shrink process.

Another particular arterial catheter for use in a cardiopulmonary bypass procedure according to the present invention is shown in two cut-away perspective views in FIGS. 3A–B. FIG. 3A shows proximal end portion (42) of elongate body (41) of arterial catheter (40) in a proximally oriented perspective view which includes a transverse cross section taken through the tubing (43) which forms the elongate body (41). FIG. 3B shows the distal end portion (62) of the same elongate body (41) in a distally oriented perspective view which includes a transverse cross section through a region of the distal end portion (62) which includes proximal internal valve (67). The particular variation shown in FIGS. 3A–B for tubing (43) which forms elongate body (41) includes a single, six lumen extrusion that includes all the lumens of the catheter shaft.

Tubing (43) forms internal flow lumen (43') which includes a proximal flow port that is schematically shown in FIG. 3A as it is proximally coupled to cardiopulmonary bypass pump (50). Internal flow lumen (43') is further shown in FIG. 3B along the distal end portion (62) of the catheter where it communicates externally of the elongate body through distal flow port (68) and intermediate flow port (66). Each of distal flow port (68) and intermediate flow port (66) are shown in FIG. 3B to include a plurality of apertures, wherein those forming distal flow port (68) include apertures along the circumference of a distal extension of tubing (43) beyond external shunt valve (70) and also an end port which terminates the lumen along the longitudinal axis. For the purpose of clarity, however, general reference to "distal flow port" in regards to the internal flow lumen is intended to herein refer to the end port and may optionally include the circumferential apertures shown in FIG. 3B. Further to the end port forming at least in part distal flow port (68), that port may also provide a means for coaxially engaging and tracking over a guidewire, as will be described in some more detail below by reference to FIGS. 11–13.

Distal and proximal internal valve actuating lumens (44, 45) are shown in FIG. 3A schematically coupled to an internal valve actuator (51) along proximal end portion (42) of elongate body (41). Internal valve actuator (51) may include a common actuator or two separate individual actuators as was previously described for the FIG. 2A variation. Distal internal valve actuating lumen (44) is further shown in FIG. 3B as it is coupled to the distal internal valve (64), shown in shadow within internal flow lumen (43') via valve coupling means (44') in the distal end portion (62) of elongate body (41). Proximal internal valve actuating lumen (45) is distally coupled to proximal internal valve (65) along the distal end portion of the elongate body via valve coupling means (45'), which is shown in cross-section through proximal internal valve (65) in FIG. 3B.

External shunt valve actuating lumen (46) is also shown in FIG. 3A as it is proximally coupled to an external shunt valve actuator (56), and is further shown in FIG. 3B as it terminates distally in inflation port (46') where it is in fluid communication with external shunt valve (70). External shunt valve actuator (56) is thus adapted to actuate expansion of external shunt valve (70) from a radially collapsed position to a radially expanded position via external shunt valve actuating lumen (46). In the expandable balloon variation shown for external shunt valve (70) in FIG. 3B, external valve actuator (56) shown in FIG. 3A is a pressurizeable fluid source which is adapted to inflate the expandable balloon by filling the balloon with fluid through external shunt valve actuating lumen (46) and inflation port (46').

Further to the expandable balloon which forms external shunt valve (70) shown in FIG. 3B, the balloon is shown to have a shape when in the radially expanded condition which forms an anchor (71) and a funnel (72). More specifically, anchor (71) is formed by a region of external shunt valve (70) which has an outer diameter when expanded that is adapted to engage an interior wall of an aorta in the region of the ascending aorta. Funnel (72) is shown in shadow to have a tapered inner surface with a proximally reducing inner diameter from a relatively large inner diameter portion, which approximates the inner diameter of the aortic root where the external shunt valve (70) is to be positioned, to a relatively small inner diameter portion, which is adjacent to and approximates the outer diameter of distal flow port (68), which may also have a plurality of apertures as shown in FIG. 3B.

Cardioplegia delivery lumen (47) and ventricular venting lumen (48) are also proximally coupled to a pressurizeable cardioplegia agent source (57) and to a decompression pump (58), respectively, as is also shown schematically along the proximal end portion (42) of elongate body (41) in FIG. 3A. These lumens are further shown in FIG. 3B as they extend distally of the distal flow port (68) where they terminate in a common cannula member in cardioplegia delivery and ventricular venting ports (not shown), also respectively.

FIG. 3C shows a more detailed, perspective view of one particular means for coupling an internal valve actuating lumen to an internal valve located within the internal flow lumen according to the various embodiments of the present invention, and is shown particularly adapted for use as proximal and distal valve coupling means (44',45') shown in FIG. 3B for the purpose of illustration.

In more detail, FIG. 3C shows elongate body (90) to include an internal valve actuating lumen (91) which has been cut-away along its distal portion such that the lumen terminates in a valve coupling port (93). An internal valve port (94) is also shown along the cut-away portion of elongate body (90) and communicates with the internal flow lumen (not shown). Internal valve (85) is adapted to the internal flow lumen and also to the internal valve actuating lumen (91) via adaption member (81).

Further detail shown in FIG. 3C for internal valve (85) includes a valve bladder (86), a valve neck (88), a lip (87), and a valve inflation port (89) which communicates with the internal cavity formed by valve bladder (86). This internal valve variation shown is of the relatively compliant type such as that described previously with reference to FIG. 2A, and preferably the individual valve components just described are formed of a uniform material, such as one molded construction.

Valve bladder (86) may be positioned within the internal flow lumen of the catheter as follows. First, a stiffening mandrel (not shown) is inserted into valve bladder (86) through valve inflation port (89) until valve bladder is stretched and distended with a sufficiently narrow width to fit within the internal valve port (94). The stiffening mandrel is then used to insert the stretched valve bladder (86) through the internal valve port (94) until lip (87) acts as a stop around the outer surface of internal valve port (94). Valve neck (88) is thereby coaxially seated within internal valve port (94) and preferably has an outer diameter which is adapted with a tight tolerance to the inner diameter of internal valve port (94), although an adhesive may also be applied to the interface in order to provide a fluid tight seal. Upon removing the stiffening mandrel, valve bladder (86) reconforms to its resting shape in the radially collapsed condition which characterizes the open position within the internal flow lumen, which shape is shown in FIG. 3C and is preferably adapted to optimize hemodynamics for blood flow therearound.

Adaption member (81) includes an adaption lumen (82) extending between a proximal adaption port (83) and a distal adaption port (84). Proximal adaption port (83) is adapted to couple to valve coupling port (93), as is shown by a schematic arrow in FIG. 3C. This adaption may be formed by potting the proximal end portion of adaption member (81) which includes proximal adaption port (83) in adhesive within internal valve actuating lumen (91). Alternatively, adaption member (81) may be comprised of an irradiated polymer, preferably an irradiated polyethylene, or still more preferably irradiated high density polyethylene, which is necked to a reduced outer diameter, then advanced within the internal valve actuating lumen (91) through port (93), and subsequently reheated and expanded to engage the interior surface of that lumen (and perhaps melt to that surface where the polymers are of compatible melt temperature).

Adaption member (81) is adapted to couple to internal valve (85) by inserting distal end portion of adaption member (81) which includes distal adaption port (84) into valve inflation port (89). Preferably a seal at this adaption is accommodated with a suitable adhesive between adaption member (81) and the interior surface of internal valve (85) within valve inflation port (89) and neck (88), particular in the case where internal valve (85) is comprised of a material which is not heat compatible with the heatshrink temperatures necessary for reconfiguring a heat memory polymer.

Figure 4C:
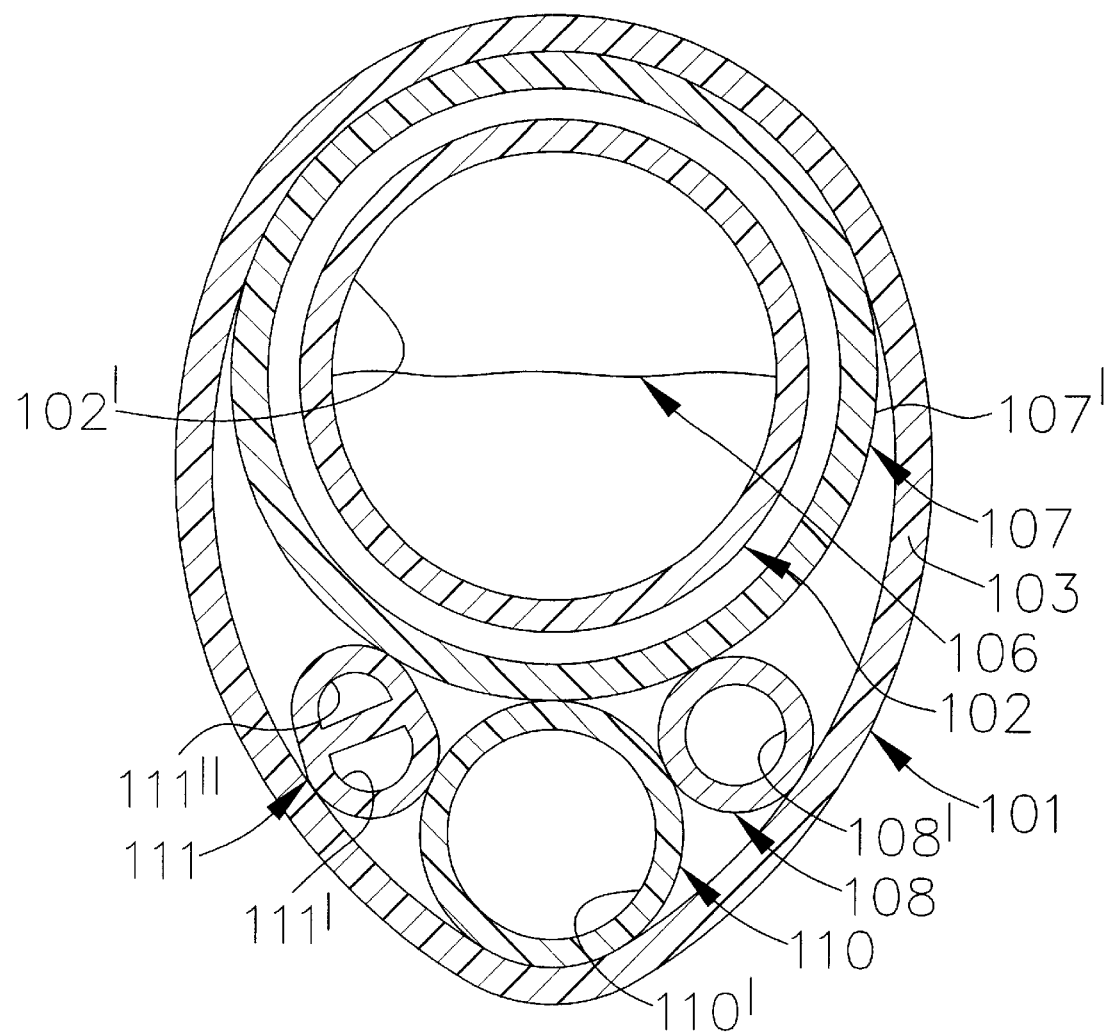
FIG. 4C shows a distally oriented transverse cross-sectional view taken along line 4C—4C through the elongate body shown in FIG. 4A.

Another arterial catheter which includes a further internal valve variation according to the present invention is shown in varied detail throughout FIGS. 4A–C. According to this further variation, an expandable member coaxially surrounds the inner tubing which forms the internal flow lumen and expands inwardly to collapse the internal flow lumen to the closed position.

In more particular detail, the distal and proximal internal valves shown in FIGS. 4A–C are formed by coaxially securing pressure cuffs (106,107), respectively, around inner tubing (102) and distally and proximally adjacent to intermediate flow port (105), which is further shown to include a plurality of apertures extending between those pressure cuffs. Distal internal valve actuating lumen (108) and proximal internal valve actuating lumen (109) are shown distally coupled to the distal and proximal internal valves, respectively, and extend proximally therefrom to a proximal end portion of the elongate body (101) where they are adapted to couple to a pressurizeable fluid source (not shown).

Further to the detail show in FIG. 4B, inner tube (102) is collapsible within the pressure cuffs (106',107') to form distal and proximal internal valves (106,107) such that the collapsed walls within those cuffs substantially occlude internal flow lumen (102') at those locations. More particularly regarding distal internal valve (106), the coaxial space between pressure cuff (106') and inner tube (102) is shown potted at each end of pressure cuff (106') with a suitable adhesive to create a seal. Further to the variation shown for proximal internal valve (107), pressure cuff (107') is comprised of a heat shrink tubing, such as has been previously herein described, which has been expanded and then shrunk at its ends to form the seal around the inner tubing. In either the adhesive or heat-shrink seal variation, the relatively coupled actuating lumen is engaged within the outer pressure cuff prior to sealing the ends of the cuff to the inner tubing, such that the final sealed internal valve is in fluid communication with a pressurizeable fluid source as a valve actuator.

For the purpose of further illustration, each of FIGS. 4B–C shows distal internal valve (106) after being pressurized and adjusted to a radially expanded condition which characterizes the closed position, wherein inner tube (102) is shown collapsed to occlude flow through internal flow lumen (102'). Proximal internal valve (107) is alternatively shown in the open position wherein internal flow lumen (102) is open and patent for fluid flow. moreover, to the extent that the coaxial space between the inner tube (102) and the outer cuff at either internal valve is expanded inwardly into internal flow lumen (102') during pressurization, this internal valve variation is herein considered a coaxial balloon variation.

One particular luminal design for the "coaxial balloon" internal valve embodiment just described is shown in various sectional perspective and transverse cross-sectional views, respectively, in FIGS. 4A and 4C. In general, outer tubing (103) coaxially surrounds and bundles inner tube (102) which forms internal flow lumen (102'), pressure cuffs (106',107') which form internal valves (106,107), distal and proximal internal valve actuating members (108,109) which form distal and proximal internal valve actuating lumens (108',109'), external shunt valve actuating member (110) which forms external shunt valve actuating lumen (110'), and cardioplegia delivery and ventricular venting member (111) which forms cardioplegia delivery lumen (111') and left ventricular venting lumen (111") (actual lumens formed by the individual tubing members are shown only in FIG. 4C).

This bundled construction just described for the arterial catheter of FIGS. 4A–C may be formed according to the heat shrink bundling process variations previously described herein. Moreover, the particular valve structures described and shown by reference to FIGS. 4A–4C should not be limited to the specific luminal construction shown in variously throughout those Figures.

Still a further arterial catheter variation according to the present invention is shown in FIG. 5A, wherein only one distal internal valve (126) is shown within the internal flow lumen (122') distally of intermediate flow port (125). This variation shown is exemplary of one further embodiment of the present invention, wherein fluid within internal flow lumen (122') proximally of intermediate flow port (125) is believed to function as a virtual proximal internal valve in the closed position. According to this variation, antegrade aortic blood flowing proximally through internal flow lumen (122') from distal flow port (124) is not allowed to pass through the internal lumen proximally of intermediate flow port (125) when there is a static head of fluid within that proximal lumen. That static head is provided when the proximal lumen is filled with the fluid and the proximal flow port (not shown) is closed. Rather, the shunted antegrade aortic flow travels out of the catheter through intermediate flow port (125).

Further to the single internal valve aspect of the FIG. 5A variation, the fluid used to fill the proximal portion of internal flow lumen (122') is preferably an isotonic and non-thrombogenic fluid, and more preferably is an isotonic saline or ringer's lactate solution. To the extent that such solution passively mixes with aortic blood near intermediate flow port (125), it may be desirable to periodically flush the proximal flow lumen through intermediate flow port (125) with additional, fresh fluid in order to clear that mixed blood component from the static column in the lumen proximally of intermediate flow port (125).

FIG. 5A also shows a particular variation for external shunt valve (140) which, similar to the particular variation shown previously in FIG. 3B, is a relatively non-compliant variation of an expandable balloon which is everted at its distal adaption to inner tube (122) which forms internal flow lumen (122'). In one method of forming the everted adaption, a balloon subassembly (not shown in detail in FIG. 5A) includes an expandable working length bordered on either end by two outwardly extending cuffs of reduced outer diameter. One of the outwardly extending cuffs is sealed around the distal end portion of the inner tube (122), thereby forming a first adaption, such that the balloon's working length extends distally therefrom. The majority of the balloon's working length is thereafter turned inside out and rolled proximally over the first adaption, until the second outwardly extending cuff is inside-out and faces proximally over the catheter shaft. The portion of the balloon's working length which is not turned inside out or rolled proximally over the first adaption is ultimately the region which forms at least a portion of funnel (142), and at least the everted, proximally extending portion of that working length forms anchor (141). A second adaption is then made between the second cuff and the inner tube (122), although proximally of an inflation port (128') through which external shunt valve actuating lumen (128) communicates with the interior chamber formed by external shunt valve (140).

The construction for elongate body (121) which forms the luminal configuration for catheter (120) is also shown in FIG. 5A, and also in additional detail in the transverse crosssectional view through elongate body (121) in FIG. 5B. In this variation, elongate body (121) includes a multi-lumen extrusion which forms internal valve actuating lumen (127), external shunt valve actuating lumen (128), and cardioplegia delivery and ventricular venting lumens (129,130), respectively. The particular variation shown for external shunt valve actuating lumen (128) actually includes two lumens which are positioned side-by-side along the circumference of the extrusion which forms larger internal valve actuating lumen (127). This particular variation is believed to optimize total luminal cross-section in order to rapidly fill and evacuate external shunt valve (140) of fluid for rapid inflation and deflation, respectively, while further minimizing the contribution of the total luminal cross-section to the outer diameter of the overall shaft assembly. Further to the multi-lumen extrusion, the individual lumens formed thereby may be cut-away for suitable adaptions where desired according to the other previous described multilumen extrusion embodiments.

FIGS. 5A–B further show inner tube (122) as it is housed coaxially within internal valve actuating lumen (127) and extends distally therefrom where it terminated in distal flow port (124). Inner tube (122) is also laminated along a relatively thin-walled interior surface of a large round lumen of the multilumen extrusion at a region along the circumference of elongate body (121) opposite external valve actuating lumen (128). This lamination maybe formed, for example, by placing an electrically conductive mandrel (not shown), such as a teflon coated stainless steel mandrel, through inner tube (122), forcing inner tube (122) with the mandrel to press against the relatively thin-walled interior surface, and then heating the mandrel such as by induction heating in order to melt the inner tube (122) to that relatively thin-walled inner surface. in this manner, a continuous space is left open between inner tube (122) and the coaxial lumen within which inner tube (122) is housed to thereby form internal valve actuating lumen (127). Further to the resultant actuating lumen, a seal is required in its distal end portion in order to pressurize that lumen for closing internal valve (126), and is shown as a heat seal in FIG. 5A at the distal region of the actuating lumen within external shunt valve (140). However, it is also further contemplated that that seal may be formed in other manners, such as for example by potting the lumen in adhesive.

Internal valve (126) is further shown in FIG. 5A to be a relatively collapsible portion of inner tube (122) and may be constructed according to several variations. In one particular variation for internal valve (126), inner tube (122) has variable thickness and is thinner at the region forming internal valve (126) where it is collapsible at a lower pressure than the rest of inner tube (122). In another variation, inner tube (122) has variable material construction along its length, wherein a more flexible and collapsible material is provided in the region forming internal valve (126). Further to this variation, inner tube may be formed generally of a high density polyethylene tubing but for the region forming internal valve (126), wherein a more is collapsible tubing such as a low density polyethylene tubing is spliced into continuous member forming inner tube (122). Still further to the variable flexibility version, inner tube may be a fiber reinforced composite, such as one containing a wire reinforcing coil or braid within a polymeric matrix, again but for the region forming internal valve (126) which is void of the reinforcing member and is therefore more amenable to collapsing under pressure.

Figure 6:
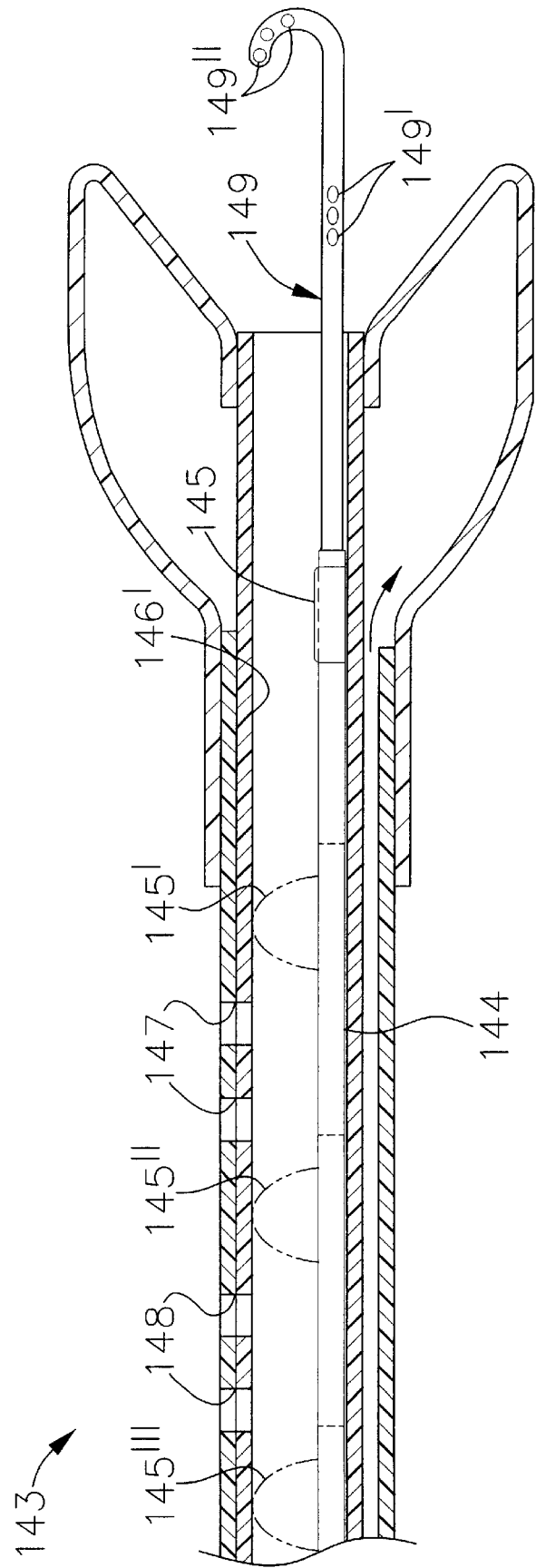
FIG. 6 shows a longitudinal cross-sectional view of another arterial catheter according to the present invention, and further shows a cannula with an adjustable internal valve which is slidably engaged within an internal flow lumen of an arterial catheter.

FIG. 6 shows still a further internal valve variation, wherein cannula (144) is slideably engaged within internal flow lumen (146') and provides internal valve (145) internally of that flow lumen (146'), rather than integrating the internal valve in a fixed arrangement along the elongate body of arterial catheter (143). According to this arrangement, the internal valve has variable positioning along internal flow lumen (146') and can be positioned for example at the following locations: distally of flow port (147), as shown at (145'); between flow port (147) and flow port (148), as shown at (145"); or proximally of flow port (148), as shown at (145'").

Still further to FIG. 6, internal valve (145) is further shown in this variation as an expandable balloon which is adjustable from a radially collapsed condition, which characterizes the open position and which allows the cannula (144) to be slideably positioned and repositioned within internal flow lumen (146'), to a radially expanded condition which characterizes the closed position. moreover, the balloon which forms internal valve (145) is also adapted to radially expand to one side of cannula (144). This design biases cannula (144) toward one side of the tubing which forms internal flow lumen (146'), thereby closing the internal flow lumen (146') with the balloon while maintaining cannula (144) in a relatively straight condition along the side of the internal flow lumen (146') in order to minimize hemodynamics affects that cannula may have on the flow through that flow lumen. Furthermore, it is believed that the internal flow lumen according to this design may be required to have a larger internal diameter in order to make up for the presence of cannula (144) and accommodate the required amount of flow therethrough. However, while internal flow lumen (146') may be enlarged for this purpose, the valve and actuating structures for the internal valve are no. longer built into the elongate body of the arterial catheter and therefore the overall profile of the assembly may not be detrimentally increased. Still further to the particular design shown in FIG. 6 for internal valve (145), other designs than a balloon may also be interchangeably constructed according to the other previously described internal valve embodiments as appropriate, such as for example according to other expandable member designs.

Moreover, cannula (144) according to the FIG. 6 embodiment may be one fixed cannula which provides the left ventricular venting lumen and cardioplegia lumen, in addition to an inflation actuating lumen for internal valve (145). Or, in the alternative, cannula (144) may provide an inflation actuating lumen for internal valve (145) and another through lumen through which one or two separate slideably cannula, such as cannula (149) shown in FIG. 6, may be engaged in order to provide the ventricular venting and cardioplegia delivery functions. According to this last arrangement, the internal valve may be desirably positioned within the internal flow lumen in order to provide the desired flow through the predetermined port or ports, while the cardioplegia delivery and left ventricular venting ports, such as ports (149',149"), respectively shown in FIG. 6, may be separately positioned through the other slideably engaged cannula or cannula.

In a further embodiment (not shown) to the "internal valve on a slidable cannula" variations just shown and described by reference to FIG. 6, the slidable cannula with the expandable member of the internal valve may alternatively be positioned within a passageway or lumen which is adjacent to the tubing which actually forms the flow lumen through the catheter, rather than actually positioning these elements within the flow lumen itself. According to this further variation, the tubing forming the internal flow lumen may be a flacid material which distends for relatively unrestricted flow under blood pressure while the valve is in the open position, and which is otherwise collapsible to occlude flow when the valve is in the closed position. Still further, the tubing forming the flow lumen may be an elastomeric tubing which elastically adjusts between collapsed and open conditions for flow according to the respective closed and open positions for the valve. These alternative constructions according to this variation are further developed above.

A further alternative external shunt valve variation to that shown and described by reference to FIG. 5A is shown in various detail and modes of operation throughout FIGS. 7A–D. According to this variation, the expandable balloon is comprised of a fiber reinforced composite which includes a predetermined, patterned mesh of relatively non-compliant fibers which are imbedded or laminated within a matrix of a relatively compliant polymeric material. A controlled and varied pattern of the reinforcing fibers along the length of the balloon is used to vary the longitudinal compliance along the balloon's length such that the funnel for the balloon valve is formed during inflation of the balloon.

More specifically, FIG. 7A shows external shunt valve (170) in a radially collapsed condition along the distal end portion of elongate body (151) of arterial catheter (150). External shunt valve (170) includes a proximal portion (171), a distal shoulder (172), and a distal taper (173). Proximal portion (171) and distal taper (173) each include similar radially oriented fibers (175) and also longitudinal fibers (176), whereas distal shoulder (172) includes similarly radially oriented fibers (175) and does not include longitudinal fibers. The longitudinal fibers (176) in proximal portion (171) and distal taper (173) are relatively non-compliant and allow for little or no longitudinal compliance to the composite balloon skin in those regions during inflation. The radially oriented fibers (175) are also relatively non-compliant, but have both a longitudinal and also a radial component to their angled orientation. Due to this angled orientation for radially oriented fibers (175), some of both the radial and also the longitudinal compliance of the matrix polymer is maintained for the composite balloon skin despite the presence of these fibers.

A progression of balloon expansion for the engineered composite variation just described is shown by comparing FIG. 7A, which shows the radially collapsed condition for exterior shunt valve (170), to FIG. 7B, which shows external shunt valve (170) in the radially expanded condition for the valve. This progression further illustrates the fiber reinforced composite variation as it forms the funnel in the shunting position according to external shunt valve of the present invention. As is shown in FIG. 7A, proximal portion (171), distal shoulder (172), and distal taper (173) have lengths L1, L2 and L3, respectively when the external shunt valve (170) is in the radially collapsed condition. Observing the relative lengths L1', L2', and L3' for the radially expanded condition shown in FIG. 7B, only distal shoulder length L2' is longer than distal shoulder length L2 due to the unique ability for distal shoulder (172) to strain longitudinally under the stress of the inflation pressure within the balloon. This variable longitudinal strain between the distal shoulder (172) and distal taper (173) produces the funnel, which is shown in further cross-sectional detail in FIG. 7C. However, because all regions of the balloon have substantially the same radial or circumferentially oriented fiber reinforcement from fibers (175), including distal shoulder (172), it is believed that a relatively constant radial compliance and therefore expanded outer diameter is provided along the working length of the balloon between the tapers, as is further shown in FIG. 7B.

Figure 8A:
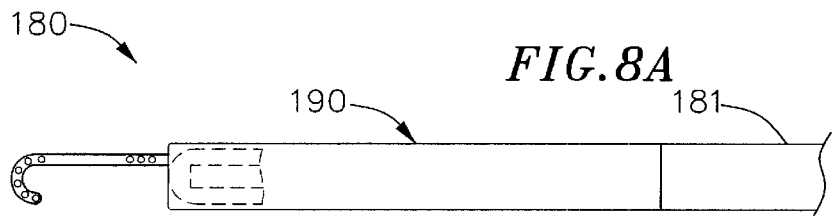
FIGS. 8A–B show perspective views of one arterial catheter according to the present invention with an external shunt valve shown in the radially collapsed and radially expanded conditions, respectively, which characterized the open and closed positions, respectively, for the valve.
Figure 8B:
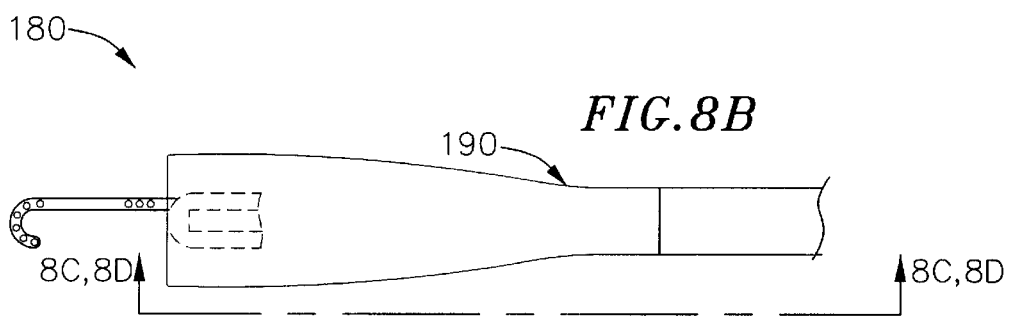
Figure 8C:
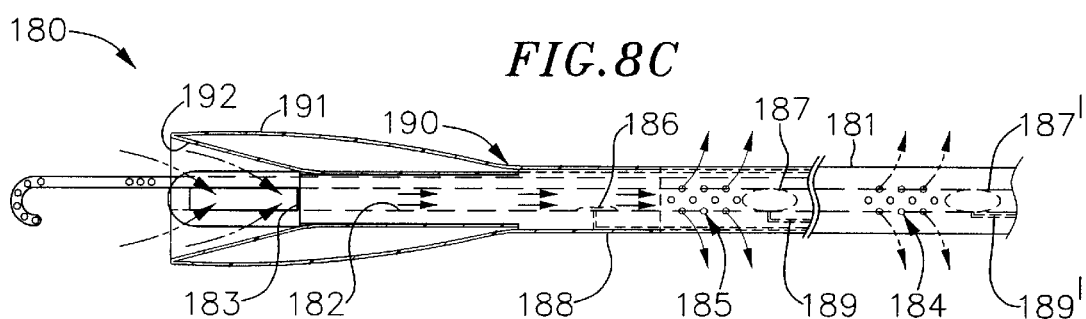
FIG. 8C shows a longitudinal cross-section taken along line 8C—8C through the arterial catheter shown in FIG. 8B, and shows internal valves adjusted to a predetermined combination of their respective open and closed positions, which combination is adapted to shunt antegrade blood flow from an aortic root distal to the external shunt valve, into the internal flow lumen through a distal flow port, and out of from the internal flow lumen through an intermediate flow port located along the elongate body proximally of the external shunt valve.
Figure 8D:
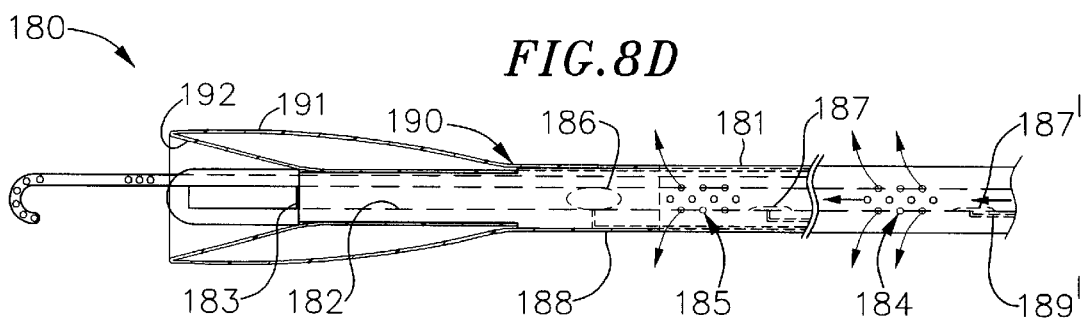
FIG. 8D shows a similar longitudinal cross-section as FIG. 8C and taken along line 8D—8D of the catheter shown in FIG. 8B, although showing the internal valves adjusted to a different predetermined combination of their respective open and closed positions, which combination is adapted to allow for distal flow of fluids through the internal flow lumen from a proximal end portion of the elongate body and out of the internal flow lumen through the intermediate flow port.
Figure 9:
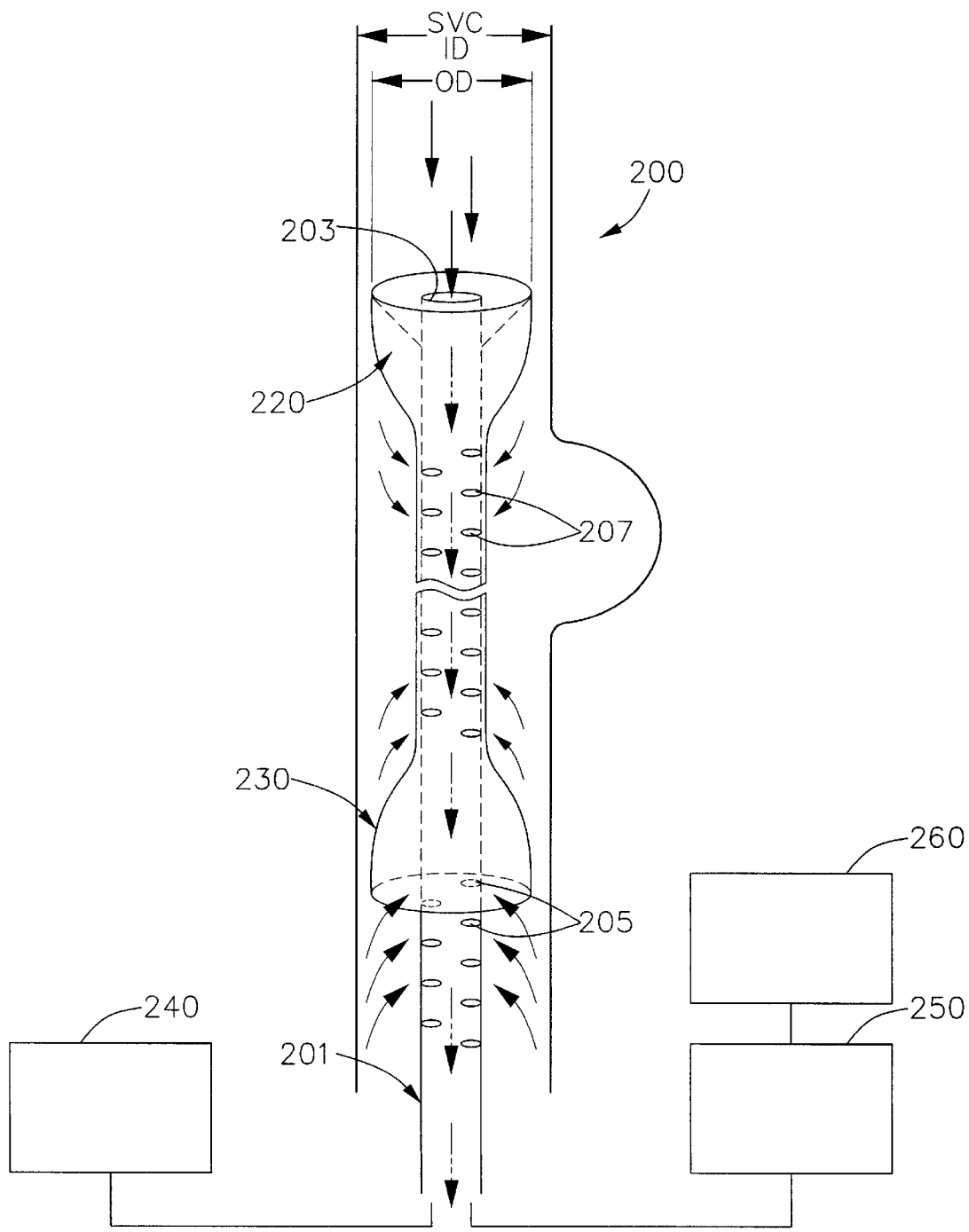
FIG. 9 shows a perspective view of a venous catheter according to the present invention during use in isolating the right ventricle from the vena cavae while aspirating venous blood from the vena cavae, proximally through an internal venous flow lumen within the elongate body of the catheter, and into the inlet port of a cardiopulmonary bypass pump which also has an outlet port coupled to an arterial catheter of the present invention.

For the purpose of further illustrating the broad functional aspects of the various particular arterial catheter embodiments just provided with reference to FIGS. 2A–6C, various views of one particular arterial catheter variation is shown throughout FIGS. 8A–D during various modes of use. FIG. 8A shows arterial catheter (180) with an external shunt valve (190) in a radially collapsed condition which characterizes the open position for the valve. FIG. 8B provides a perspective view of arterial catheter (180) with the external shunt valve (190) adjusted to the radially expanded condition which characterizes the closed position for the valve. Detailed modes for adjusting the internal valves within arterial catheter (180), during radial expansion of external shunt valve (190) in the closed position, are shown in FIGS. 8C–D. FIG. 8C shows arterial catheter (180) during one operational mode which is adapted to shunt antegrade aortic blood flow from the aortic root (distally to the expanded external shunt valve), through an internal flow lumen within the catheter, and out of that flow lumen and into the systemic arterial circulation at a proximal region of the aortic artery. According to this mode, distal internal valve (186) is in the open position and proximal internal valve (187) is in the closed position. Antegrade aortic blood is depicted by arrows as it enters the funnel (192) formed by external shunt valve (190), through distal flow port (183), along internal flow lumen (182), and out intermediate flow port (185) proximally of external shunt valve (190).

The same arterial catheter (180) is further shown in FIG. 8D after adjusting the external and internal valves to another predetermined combination of their respectively open and closed positions such that the catheter is adapted to isolate the systemic arterial circulation from the aortic root distally to the external shunt valve (190) and also distally of the distal internal valve (186) within internal flow lumen (182). The valving configuration of FIG. 8D further adapts arterial catheter (180) to provide retrograde flow of oxygenated blood from a cardiopulmonary bypass pump (not shown), distally through the internal flow lumen (182), and into the systemic circulation proximally of the external shunt valve (190). This combination of valve adjustments is shown to include adjusting external shunt valve (190) to the shunting position, distal internal valve (186) to its closed position, and proximal internal valve (187) to its open position.

A second intermediate flow port (184) is also shown in shadow in FIGS. 8C–D and is optionally provided according to the arterial catheter mode of the present invention, as was its previously described. Concomitant with the inclusion of second intermediate port (184), proximal internal valve (187) becomes an intermediate internal valve by virtue of its position between the adjacent pair of intermediate flow ports (185,184). Proximal internal valve (187') is thus provided proximally of second intermediate flow port (184), as is shown in shadow in FIGS. 8C–D. The inclusion of second intermediate flow port (184) in the perfusion of oxygenated blood through the catheter is shown in both the antegrade aortic flow and retrograde bypass flow scenarios with dashed lined arrows in FIGS. 8C–D, respectively. As was previously described, the antegrade aortic flow through both intermediate flow ports as shown in FIG. 8C is achieved by closing proximal internal valve (187') and opening distal internal valve (186) and proximal internal valve (187), which in this case is actually an intermediate internal valve. The alternative blood perfusion from the bypass pump as shown in FIG. 8D is permitted through the second intermediate flow port by opening proximal internal valve (187') and either closing proximal internal valve (187), which isolates perfusion flow through only the second intermediate flow port (184), or opening internal valve (187) and closing distal internal valve (186), which perfuses the blood from the pump through both the intermediate flow ports (185,184).

Venous Catheter

The venous catheter mode of the present invention is generally adapted to isolate the right heart from vena caval blood flow and to aspirate that flow into a cardiopulmonary bypass pump without circumferentially engaging the interior wall of the vena cavae. Specific embodiments of this mode are shown and described in detail in FIG. 9 and FIGS. 10A–D.

One venous catheter variation which is adapted to substantially isolate the right heart chambers from the venous flow in the vena cavae and which achieves this isolation without engaging the walls of the vena cavae is shown during use in a vena cavae in FIG. 9. More specifically, venous catheter (200) includes an elongate body (201) which includes a distal flow port (203) located along the elongate body's distal end portion and an intermediate flow port (205) located along the distal end portion proximally of distal flow port (203). A distal external valve (220) is located along the distal end portion proximally adjacent to distal flow port (203), while an intermediate external shunt valve (230) is positioned distally adjacent to intermediate flow port (205).

Each of the distal and intermediate external valves (220, 230) shown in the FIG. 9 variation is adjustable from a radially collapsed condition, which characterizes an open position, to a radially expanded condition, which characterizes a closed position. The respective open positions for these valves is adapted to allow for percutaneous transluminal delivery of the elongate body's distal end portion into the region of the vena cavae adjacent to the sinus venarum in the right heart, and is also adapted to allow for venous blood flow to pass from the superior and inferior vena cava and into the right heart chambers through the sinus venarum or vena caval inlet where the vena cavae communicate with the right atrium. The alternatively closed positions for the distal and intermediate external valves (220,230) is adapted to substantially isolate the right heart chambers from vena caval blood flow and aspirate that flow into a cardiopulmonary bypass pump, as is described in more detail below.

FIG. 9 shows each of the distal and intermediate external valves (220,230) in the radially expanded condition which characterizes its respective closed position. Each of the valves in the radially expanded condition has a working length with an outer diameter which is slightly less than the inner diameter of the superior vena cava, in the case of distal external valve (220), or the inferior vena cava, in the case of intermediate external valve (230). This relationship is shown for example in FIG. 9 by comparing distal external valve outer diameter OD with superior vena cava inner diameter SVC ID. The closed position for the valves therefore does not completely occlude the relative vena cava, but instead only substantially occludes the vessel lumen and thereby increases the pressure upstream of the respective valve. By positioning each valve downstream and adjacent to a flow port into an internal lumen of the catheter, the increased pressure due to the valve expansion thereby increases the pressure adjacent to the adjacent flow port and enhances aspiration of blood through that port and into the respectively coupled internal flow lumen. The aspirated blood further travels proximally along the flow lumen, out of the lumen through a proximal flow port (not shown), and into a cardiopulmonary bypass pump, shown schematically at cardiopulmonary bypass pump (250), which may be any suitable pump such as the "BioPump" described above, according to one of ordinary skill.

The external valves shown and described for the venous catheter variation of FIG. 9 therefore do not completely isolate the right heart chambers from vena caval blood, but instead do so only substantially by creating a significant occlusion to flow into those heart chambers and aspirating the blood with suction from an external pump at a location opposite that artificial occlusion from the heart. However, it is contemplated that the "substantial" aspiration of blood and "substantial" isolation of the heart may still provide some degree of leakage of vena caval blood around the external valves and into the heart.

Further to the external valve leakage just described, a leakage flow port (207) is further shown in FIG. 9 between distal external valve (220) and intermediate external valve (230). Leakage flow port (207) enhances additional aspiration of the blood which might leak around the distal and intermediate external valves (220,230) and into the region of the vena cava adjacent to the sinus venarum.

It is believed that each of the distal, intermediate, and leakage flow ports (203,205,207) preferably communicate proximally to the cardiopulmonary bypass pump via independent and separate flow lumens. For example, a distal flow lumen (not shown) may fluidly couple a distal flow port (203) to a proximal flow port (not shown) which is coupled to cardiopulmonary bypass pump (250)(proximal flow port coupling shown schematically), an intermediate flow lumen (not shown) may fluidly couple intermediate flow port (205) to cardiopulmonary bypass pump (250), and a leakage flow lumen (not shown) may couple leakage flow port (207) to cardiopulmonary bypass pump (250). Further to such a multiple venous aspiration luminal design, it is farther believed that a higher negative pressure may be desirable at the the the distal flow port (203) than the other ports. Moreover, another acceptable variation provides a common internal flow lumen (not shown) between distal and intermediate flow ports (203,205), with a separate independent flow lumen (not shown) coupled to leakage flow port (207).

According to this latter variation, the blood which leaks around and between distal and intermediate external valves (220,230) and which is adjacent to leakage flow port (207) is at a significantly lower pressure than the blood adjacent the distal and intermediate flow ports (203,205) on the upstream side of either of external valves (220,230), respectively. If leakage flow port (207) were coupled to the same internal flow lumen as distal or intermediate flow ports (203,205), such a coupling may provide a shunt around the external valves and cause an undesirable flow of blood from the high pressure zones adjacent to distal and intermediate flow ports (203,205), through the common internal flow lumen, and outwardly into the low pressure zone through leakage flow port (207). By segregating the internal flow coupled to leakage flow port (207) from the internal flow lumen coupled to the other high pressure flow ports, the relatively low pressure flow is isolated from the relatively high pressure flow.

Further to the FIG. 9 variation, it is further contemplated that distal external valve (220) may be provided at the exclusion of intermediate internal valve (230). The venous blood pressure in the inferior vena cava is lower than that in the superior vena cava, and it is believed that the blood in the inferior vena cava may be sufficiently aspirated merely through applied suction from the external pump at intermediate flow port (205). In the higher pressure zone at the superior vena cava, however, it is believed that at least a partially occlusive cuff such as distal external valve (220) may be required in order to prevent unacceptably high volumes of blood from flowing past the distal flow port (203) and entering the right heart chambers.

For the purpose of further illustrating the use of venous catheter (200) in a minimally invasive cardiac bypass system, FIG. 9 further shows cardiopulmonary bypass pump (250) schematically coupled to arterial catheter (260) via an outlet port (not shown) on the pump. Arterial catheter (260) is generally adapted to isolate the left heart chambers from systemic arterial circulation while perfusing oxygenated blood from the cardiopulmonary bypass pump (250) into that circulation. Furthermore, arterial catheter (260) may comprise one of several conventionally known catheters for this purpose, or may include one of the several arterial catheter embodiments previously described above according to the present invention. In addition, FIG. 9 also schematically shows the proximal end portion of venous catheter (200) as it is proximally coupled to an external valve actuator (240). External valve actuator (240) is adapted to adjust the external valves along the distal end portion of the catheter between their relative open and closed positions. External valve actuator (240) may be specifically adapted as one pressurizeable fluid source adapted to switch actuation between the external valves, in the case of expandable balloon variations provided at the external valves, or alternatively as two such fluid sources, as has been previously described above for adjusting multiple balloons as internal valves.

The present invention according to the FIG. 9 variation further contemplates other designs for external valves along the venous catheter body which are adapted to substantially isolate the right heart chambers from vena caval blood flow without circumferentially engaging the interior wall of the vena cavae. For example, in one further vena caval example (not shown), regions along the distal end portion of the elongate body for the venous catheter may include suction ports which are adapted to provide sufficient negative pressure adjacent to the vena caval wall that the wall collapses down around the elongate body at that region. This "suction region" may have a larger outer diameter than the other portions of the venous catheter in order to minimize the extent to which the vena caval wall must collapse. Furthermore, such a "suction region" may also be expandable to an expanded outer diameter which approaches the inner diameter of the vena caval wall, although falling short of actually engaging the wall. Upon collapsing the vena caval wall onto the body surface adjacent to the ports along the suction region, the expandable section may remain at the expanded outer diameter, or may alternatively be reduced in its outer diameter, bringing the vena caval wall further downward to a reduced diameter.

Another alternative venous catheter variation to that shown in FIG. 9 is shown in FIGS. 10A–D, wherein venous catheter (250) is shown in various modes of operation as it is adapted to isolate a right ventricle from vena caval flow without engaging the interior walls of the vena cavae.

Figure 10A:
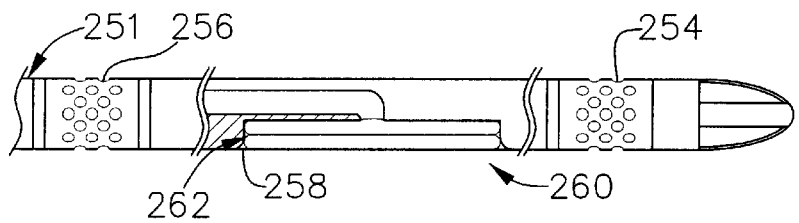
FIG. 10A shows a perspective view of another venous catheter according to the present invention, and further includes a sectioned longitudinal cross sectional view through the catheter in the region of an external valve which includes a valve member that is shown in a first radial position which characterizes an open position for the external valve.

As shown in FIG. 10A, venous catheter (250) includes an external valve (260) along the distal end portion of elongate body (251) between distal and proximal flow ports (254, 256). External valve (260) includes a valve member (262) which is positioned at a discrete location around the circumference of elongate body (251) and is shown in FIG. 10A in a first radial position which characterizes the open position for external valve (260). In the particular variation shown, valve member (262) in the first radial position is housed within a recess (258) provided at the discrete location along the elongate body's circumference. In this open position, external valve (260) is therefore adapted to facilitate percutaneous transluminal delivery of the distal end portion of elongate body (251) into the region of the vena cavae adjacent to the sinus venarum, and is further adapted to allow for venous flow to perfuse around the elongate body's distal end portion and into the right heart chambers.

Distal and intermediate flow ports (254,256) are coupled to at least one internal flow lumen which extends through the catheter and terminates proximally in a proximal flow port which couples to an inlet port of a cardiopulmonary bypass pump (not shown). Any one of several variations for coupling these ports to the proximal pump may be suitable, as was previously described by reference to the prior venous catheter shown in FIG. 9.

Figure 10B:
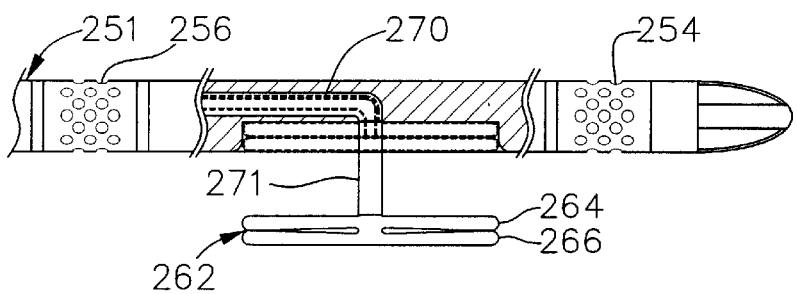
FIG. 10B shows a similar sectional perspective view of the venous catheter shown in FIG. 10A, although showing the valve member of the external valve after being actuated from the first radial position to a radially displaced position which is adjacent to the elongate body.

FIG. 10B shows venous catheter (250) in a further operational mode, wherein valve member (262) has been adjusted from the first radial position to a radially displaced position which is adjacent to the outer surface of elongate body (251). When the discrete location of valve member (262) is positioned within the vena cavae and adjacent to the sinus venarum into the right atrium, the radially displaced position for valve member (262) is adapted to place valve member (262) within the right atrium, preferably at or adjacent to the tricuspid valve which separates the right atrium from the right ventricle.

Valve member (262) is further shown in FIGS. 10A–B to include two expandable members (264,266), which are each adjustable from a radially collapsed condition (shown in FIGS. 10A–B) to a radially expanded condition. Expandable members (264,266) are further shown in FIG. 10C to be coupled to expandable member actuators (271,272). In the particular variation shown variously throughout FIGS. 10A–B, expandable members (264,266) are balloon members which are adjusted to the radially expanded position by pressurizing their inner chamber with fluid. Such balloon construction may be of the relatively compliant type or of the relatively non-compliant type, as have been described previously above. According to the expandable balloon variation, expandable member actuators (271,272) therefore comprise luminal passageways which are adapted to couple to at least one pressurizeable fluid source (not shown) for inflating the respectively coupled balloon or balloons. It is contemplated that either one such pressurizeable fluid source may be coupled to both expandable members (264,266), or separate such sources may be provided for individually actuating each expandable member (264,266), respectively.

Figure 10C:
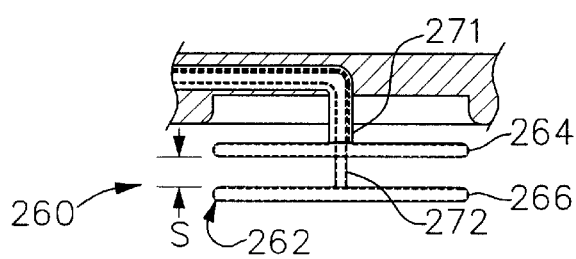
FIG. 10C shows a longitudinal cross-sectional view of the external valve shown in FIGS. 10A–B, although further showing two expandable members of the valve member which are separated by a space.
Figure 10D:
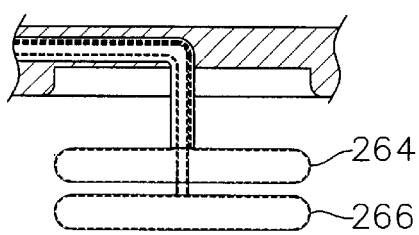
FIG. 10D shows a similar longitudinal cross-sectional view of the external valve shown in FIG. 10C, although showing each of the two expandable members further adjusted to a radially expanded condition which narrows the space therebetween and, when the tricuspid valve is positioned within the space, characterizes the closed position for the valve member.

FIG. 10C further shows expandable members (264,266) separated by a space S. This separation may be a fixed relationship between the members, or may be adjustable. One variation of the latter adjustable arrangement is shown in FIG. 10C, wherein expandable members (264,266) are independently adjustable and moveable relative to the other by manipulating the respectively coupled expandable valve actuator. One suitable construction for this adjustable separation variation for the expandable members may provide a groove through or around expandable member (264) so that expandable member actuator (272) may slideably extend through the groove to adjust the positioning of the more distally disposed expandable member (266). In another construction, expandable member actuator (272) may be coaxially disposed within expandable member actuator (271) and also within and through expandable member (264).

In one more particular variation of this latter construction (not shown), expandable member actuator (271) is preferably constructed of an inner member coaxially disposed within and extending distally beyond an outer member. Expandable member (264) is sealed at its proximal end upon the outer member and at its distal end upon the inner member. The coaxial space between the inner and outer member provides the inflation lumen for expanding expandable member, whereas the inner lumen formed by the inner member forms an inner conduit through which expandable member actuator (272) may slideably extend through and distally beyond for coupling to expandable member (266).

The distal end portions of expandable member actuators (271,272) must advance along and bend through a substantial angle while adjusting the valve member (262) from the first radial position shown in FIG. 10A to the radially displaced position shown in FIGS. 10B–D. Therefore, these actuators are preferably highly flexible, and comprise for example highly flexible polymeric tubing for the expandable member balloon variation shown. Examples of acceptable materials for constructing these actuator tubings include for example: low modulus polyurethane, PEBAX, low or linear low density polyethylene, nylon, and polyvinyl chloride. In order to achieve the requisite pushability and remote maneuverability of the distal end portions, however, the proximal end portions of expandable member actuators (271,272) (not shown) may be preferably constructed of stiffer materials, such as for example high density polyethylene, high modulus polyurethane, polyester terepthalate, polyimide, or metal hypotube materials, in order to allow for distal advancement of those members through elongate body (250) such that expandable members (264,266) for valve member (262) may be adjusted to the relatively displaced positions described.

FIG. 10D shows expandable members (264,266) during still a further mode of operating venous catheter (250) and after being adjusted from the radially collapsed condition shown in FIGS. 10A–C to a radially expanded condition. This radially expanded condition of expandable members (264,266) substantially reduces or closes the space S between those members (shown in FIG. 10C), and is adapted to engage the tricuspid valve when positioned within that space prior to expanding the expandable members.

Therefore, according to the progressive modes of operation shown for particular venous catheter (250) in FIGS. 10A–D, the closed position for the external valve (260) is characterized by: (1) aligning the discrete location of valve member (262), while in the first radial position within recess (258), with the sinus venarum in the right atrium; (2) adjusting valve member (262) from the first radial position to the radially displaced position adjacent to elongate body (251) and at least in part within the right atrium and adjacent to the tricuspid valve between the right atrium and the right ventricle; and (3) adjusting at least a portion of the valve member (262) from a radially collapsed condition to a radially expanded condition which engages the tricuspid valve and substantially isolates the right ventricle from the vena cava.

It is further contemplated that other venous catheter variations than those just shown and described by reference to FIGS. 9–9D may suitably function as the venous catheter of the present invention which is broadly adapted to: (a) substantially isolate the right ventricle from the venous blood flow; and (b) substantially aspirate the vena caval blood into a cardiopulmonary bypass pump; and wherein both the isolation and the aspiration functions are performed without circumferentially engaging the interior wall of the vena cavae.

For example, in a further variation (not shown) of the external valve shown variously throughout FIGS. 10A–D, the valve member in the radially displaced position expands within the right atrium and fills that atrium to such an extent that either no blood or a negligible volume of venous blood is allowed to flow between the vena cavae and the right ventricle. In a further variation of the discretely located and radially displaced valve member, the valve member in the radially expanded condition circumferentially engages a circumferential path of atrial wall tissue which defines that atrium, thereby transecting the atrium such that the sinus venarum is isolated from the right ventricle by the expanded valve member. In still a further variation, the two expandable members are substantially provided as previously shown and described by reference to FIGS. 10A–D, although are modified to instead engage the internal valve and thereby isolate the right ventricle simply by adjusting the individual members toward each other—in other words, the expandability of the expandable members may not be completely required.

Minimally Invasive Bypass Catheter System

FIGS. 10–14 show one minimally invasive cardiac bypass system which includes one combination of particular arterial and venous catheter embodiments previously described above for the purpose of further illustrating the sequential modes of use of the combination assembly in performing a minimally invasive cardiac bypass procedure according to the present invention. For example, venous catheter (320) shown throughout FIGS. 10–14 is constructed according to the particular embodiment previously shown and described by reference to FIGS. 10A–D. However, other venous catheter embodiments such as that previously described by reference to FIG. 9 may be alternatively suitable for use in the overall assembly shown in FIGS. 10–14.

FIGS. 10–14 further show highly schematic representations for the aortic artery, superior and inferior vena cavae, and heart within which the catheters of the overall assembly are shown in various operable modes. For example, there is no particular depiction of the left or right atria or ventricle, although the salient structures regarding the operable catheter modes shown are provided schematically, including the sinus venarum and tricuspid valve in the right heart and the aortic valve in the left heart.

More specifically, FIG. 11 shows the arterial and venous catheters (301,320) which make-up minimally invasive cardiac bypass catheter system (300) during placement within their respectively desired target vessels. Such percutaneous transluminal catheter placement may be performed in-part according to the standard "Seldinger" technique or according to a direct "cut-down" method including an arteriotomy, as would be apparent to one of ordinary skill. For the purpose of further illustration, however, the general access method according to the "Seldinger" technique is performed as follows.

First, a puncture is first made in the desired vessel for introducing the subject catheter. Such an introduction site for the arterial catheter may be for example in a femoral or a subclavian artery, although preferably in the femoral artery, and for the venous catheter may be for example in a femoral or jugular vein, although preferably in a femoral vein. A guidewire is then advanced through the bore of the needle, after which the needle is withdrawn and a dilator is advanced coaxially over the guidewire. By advancing a tapered distal end of the dilator through the puncture site, that wound is dilated open by the taper until reaching a desired predetermined diameter. An introducer sheath with a hemostatic valve is then advanced either over the dilator or the guidewire or both, after which either the dilator or the guidewire or both are removed from the introducer. The subject device is then advanced into the relative vessel coaxially through the introducer sheath and hemostatic valve.

Each of the venous and arterial catheters is also adapted to track over a steerable, radiopaque guidewire which is adapted to steer and select desired branched vessels under X-Ray visualization in percutaneous transluminal procedures. Therefore, FIG. 11 shows arterial catheter (301) and venous catheter (320) while tracking over guidewires (310, 315), respectively, and into the aortic arch and the region of the vena cavae adjacent to the sinus venarum of the right heart, also respectively. Each of guidewires (310,315) may be coaxially positioned within the internal flow lumen and through the proximal and distal flow ports of the respectively engaged catheter. Alternatively, each of these guidewires may be slideably engaged within a common internal flow lumen which extends between and fluidly couples with a distal and intermediate flow port along the distal end portion of the respective catheter, such as for example in "rapid-exchange" or "monorail" catheter designs which are previously disclosed for use in angioplasty catheters. In still another alternative variation, the guidewires may be slideably disposed within separate guidewire tracking members extending throughout the respective arterial and venous catheters. Regardless of the particular catheter coupling, however, any one of several known guidewire designs may be suitable for use in positioning the catheters of the present invention, as would be apparent to one of ordinary skill.

Further to the positioning mode of operation shown in FIG. 11, both external shunt valve (303) and external valve (330) are shown in their respectively closed positions which allow for the arterial or venous blood to flow around the distal end portion of the respective arterial and venous catheters (301,320) and which also allow for the percutaneous transluminal placement according to this mode. Further to the placement of arterial catheter (301), the distal end portion of elongate body (301) is placed within the aortic arch such that external shunt valve (303) is positioned between the aortic root and the carotid arteries. The distal end portion of elongate body (322) for venous catheter (320) is positioned such that distal flow port (324) and intermediate flow port (326) are positioned within the superior and inferior vena cavae, respectively, and such that valve member (332) for external valve (330) is aligned with the sinus venarum in the right atrium.

In order to facilitate accurate positioning as just described for the relative components along the distal end portions of the arterial and venous catheters, radiopaque markers may be provided at or adjacent to these catheter structures in order to use X-ray or fluoroscopic visualization when guiding the catheters into place. In the alternative or in addition to such radiopaque markers, markers or other indicia may also be provided on the proximal end portions of these catheters such that the catheters in vivo position is determinable when the catheter is observed to advance a predetermined distance beyond an introducer sheath or guiding catheter according to the positioning of such proximal indicia relative to the introducer or guiding catheter. Moreover, the present invention further contemplates use of other positioning means in order to accurately place the relative valves and flow ports of the arterial and venous catheters. For example, ultrasound visualization may be used to aid in accurate placement of these structures. In one ultrasound variation, an ultrasonic probe may be used externally of one or both of these catheters, either along side and adjacent to the catheter or even further removed location such as in the esophagus in a transesophageal approach. Still further, direct fiber optic imaging may be employed for visualizing the position of the respective catheter structures in relation to the particular anatomical structures of interest.

FIG. 12 shows a further mode of operation for each of arterial and venous catheters (301,320) during use within minimally invasive cardiac bypass system (300).

More specifically to arterial catheter (301) as shown in FIG. 12, exterior shunt valve (303) is shown in a radially expanded condition which characterizes a shunting position for that valve within the aortic arch. Exterior shunt valve (303) in the shunting position forms anchor (304), which circumferentially engages the interior surface of the aortic wall, and also forms funnel (305) which directs antegrade aortic blood flow into distal flow port (306), proximally through an internal flow lumen (not shown) and out an intermediate flow port (307) which is located along elongate body (302) proximally of external shunt valve (303). In this operable mode, arterial catheter (301) is thus adapted to secure the distal end portion of elongate body (302) into position while allowing the heart to continue beating and perfusing the systemic arterial circulation proximally of anchor (304). This shunted antegrade flow may be further facilitated by adjusting a distal internal valve (not shown) within the flow lumen distally to intermediate flow port (307) and a proximal internal valve (not shown) within the flow lumen proximally of intermediate flow port (307) to open and closed positions, respectively, as has been previously described above by reference to the particular arterial catheter embodiments.

Further to the operable mode of arterial catheter (301) shown in FIG. 12, a distal cannula member is shown extending from elongate body (302) distally from external shunt valve (303) and distal flow port (307), and includes cannula delivery port (308) and ventricular venting port (309). Cannula delivery port (308) is positioned within the aortic root in the region of the sinus of valsalva and is fluidly coupled to a pressurizeable cardioplegia agent source (not shown) via a cardioplegia delivery lumen (also not shown), such as has been described previously above.

Ventricular venting port (309) is positioned through the aortic valve and into the left ventricle where it is adapted to aspirate residual blood from that ventricle during the cardiac bypass procedure.

Specifically regarding venous catheter (320) as shown in FIG. 12, valve member (332) is shown adjusted to a radially displaced position adjacent to the elongate body (322) and within the right heart chambers. In more detail, two expandable members (334,336) which comprise at least in part valve member (332) are separated by a space which houses the tricuspid valve located between the right atrium and ventricle.

FIG. 13 shows still a further operable mode for each of the arterial and venous catheters (301,320) as they are used to bypass the heart subsequent to temporarily arresting the heart according the overall assembly of the current invention.

Arterial catheter (301) is shown in an operable mode where it is adapted to isolate the heart from systemic arterial circulation and provide artificial flow of oxygenated blood into the systemic circulation from the cardiopulmonary bypass pump (not shown). According to this mode, cardioplegia agent is delivered into the coronary arteries via cardioplegia delivery port (308) and the heart is thereby temporarily arrested. With external shunt valve (303) still anchored in the aortic arch in the shunting position, the internal lumen is selectively occluded with a distal internal valve (not shown) located within the lumen between the distal and intermediate flow ports (306,307) according to the operable mode shown in FIG. 13. Thus, the left heart chambers are isolated from systemic arterial circulation proximally of external shunt valve (303) and the distal internal valve within the internal flow lumen. Arrows exiting intermediate flow port (307) are thus used in FIG. 13 to depict the artificial flow of oxygenated blood distally through the internal flow lumen from a cardiopulmonary bypass pump.

Venous catheter (320) is shown in FIG. 13 in an operable mode which is adapted to substantially isolate the right heart chambers from the vena cavae and also to aspirate the venous blood in the vena cavae into the inlet port of the cardiopulmonary bypass pump. According to this mode, the two expandable members (334,336) are shown adjusted to a radially expanded condition which narrows the space of separation therebetween and engages the tricuspid valve, thereby isolating the right ventricle from the right atrium and vena cavae. Arrows show venous blood as it is aspirated into the at least one internal flow lumen of the venous catheter and into a cardiopulmonary bypass pump (not shown).

The structural features of the various individual catheter embodiments described above should not be limited to use in minimally invasive cardiac bypass assemblies or procedures, and may be adapted according to one of ordinary skill for other medical applications without departing from the scope of the present invention. In particular, systems which utilize one or several of the arterial and venous embodiments described above may be used in either open heart applications, wherein a surgeon uses the catheters provided for isolating the heart but nevertheless performs a sternotomy for direct surgical access to the heart, "port-access" types of procedures, or even still more minimally invasive procedures wherein the heart is isolated by use of the catheters of the present invention and further medical treatment is also performed via percutaneous translumenal assemblies and methods.

In a further example, an external shunt valve which forms an anchor and a funnel for directing flow through an internal catheter lumen, although specifically provided above in catheter embodiments which are adapted for shunting antegrade aortic blood flow into the systemic arterial circulation, may also be modified for applications within other lumens or body spaces and still fall within the scope of the present invention. Furthermore, other catheter applications than those described above for use in an aorta may include the internal valve embodiments herein described for selectively opening or closing an internal flow lumen and still fall within the scope of the present invention.

In still a further example, catheters which are generally adapted to isolate one body space or lumen from another body space or lumen by adjusting a valve member from a first radial position at a discrete location around the catheter's circumference to a radially displaced position which is adjacent to the elongate body of the catheter are considered within the scope of the present invention, notwithstanding the specific description above which provides such a valve member only on a venous catheter in a minimally invasive cardiac bypass system.

Other modifications or combinations of the specific catheter embodiments described above which may become apparent to one of ordinary skill from this disclosure, but which have not been specifically described herein, are also contemplated as falling within the scope of the present invention. In addition, improvements to the embodiments which are not specifically provided for but which may be apparent to one of ordinary skill based upon this disclosure are also included within the invention, such as for example an improvement providing a heparin coating on an external or internal surface on any one of the arterial or venous catheter embodiments.

What is claimed is:

1. A medical device assembly for aspirating a volume of venous blood from at least one of a superior or inferior vena cava adjacent to a heart while substantially isolating a right ventricle of the heart from the vena cavae, the heart including the right ventricle, a right atrium, and a sinus venarum through which the vena cavae communicate with the right atrium, the assembly comprising:

an elongate body with a proximal end portion, a distal end portion, and a flow lumen that extends between a distal flow port located along the distal end portion and a proximal flow port located along the proximal end portion, the distal end portion being adapted for retrograde percutaneous transluminal delivery into a region of the vena cavae adjacent to the sinus venarum such that the distal flow port is positioned within the superior vena cava, and the proximal flow port being adapted to couple to an inlet port of a cardiopulmonary bypass pump;

an external valve which is located along the distal end portion proximally of the distal flow port and which is adjustable from a closed position, which is adapted to allow a volume of venous blood to flow from the superior vena cavae, through the sinus venarum into the right atrium, and into the right ventricle, to an open position, which is adapted to substantially isolate the right ventricle from the superior and inferior vena cavae without circumferentially engaging an interior surface of either of the superior or inferior vena cavae; and an external valve actuator with a proximal end portion and a distal end portion that is coupled to the external valve, and which is adapted to selectively adjust the external valve between said open and closed positions.

2. The medical device assembly of claim 1, wherein said external valve further comprises a valve member which is located at a discrete location along a circumference of the elongate body and which is adjustable from a first radial position to a radially displaced position which is located adjacent to the elongate body, whereby the closed position for the external valve is at least in part characterized by aligning the discrete location of the valve member with the sinus venarum such that the valve member in the radially displaced position is located at least in part within the right atrium.

3. The medical device assembly of claim 2, wherein the valve member further comprises two separate members which are adjustable from a first relative position, wherein the two separate members are separated by a space, to a second relative position, wherein the space is substantially narrowed.

4. The medical device assembly of claim 3, wherein at least one separate member is expandable from a radially collapsed condition, which at least in part characterizes the first relative position, to a radially expanded condition, which at least in part characterizes the second relative position; and further comprising an expansion actuator having a proximal end portion and a distal end portion which is coupled to the at least one separate member and is adapted to adjust the at least one separate member from the radially collapsed condition to the radially expanded condition.

5. The medical device assembly of claim 4, wherein the at least one separate member further comprises an expandable balloon, and wherein the expansion actuator further comprises an expansion actuating lumen extending between the distal and proximal end portions of the expansion actuator, the expansion actuating lumen in the distal end portion of the expansion actuator being fluidly coupled to the expandable balloon, and the expansion actuating lumen in the proximal end portion of the expansion actuator being adapted to fluidly couple to a pressurizeable fluid source.

6. The medical device assembly of claim 3, wherein at least one of the two separate members is moveable with respect to the other separate member; and further comprising an actuator with a proximal end portion and a distal end portion which is adapted to move the at least one separate member relative to the other;

whereby moving the at least one separate member relative to the other adjusts the two separate members from the first relative position to the second relative position.

7. The medical device assembly of claim 1, said external valve further comprising:

an expandable member which is adjustable by said external valve actuator from a radially collapsed condition, which characterizes at least in part the open position, to a radially expanded condition wherein the expandable member has an outer diameter which substantially occludes the superior vena cava but is less than an inner diameter of the superior vena cava.

8. The medical device assembly of claim 7, wherein said elongate body further comprises an intermediate flow port which is located proximally of the external valve and is adapted to be positioned within the inferior vena cava when the distal flow port is positioned within the superior vena cava, said intermediate flow port being in fluid communication with either the flow lumen or an intermediate flow lumen which extends between the intermediate flow port and a second proximal flow port which is located along the proximal end portion of the elongate body and which is adapted to couple to an inlet port of a cardiopulmonary bypass pump.

9. The medical device assembly of claim 8, wherein the external valve is a distal external valve, and further comprising:

an intermediate external valve which is located along the distal end portion of the elongate body distally of the intermediate flow port and also proximally of the distal external valve such that the distal and intermediate external valves are adapted to be positioned within the superior and inferior vena cavae, respectively, said intermediate external valve also being adjustable from an open position, which is adapted to allow for a volume of blood to flow from the inferior vena cava and through the sinus venarum into the right atrium and ventricle, to a closed position, which is adapted to substantially isolate the right atrium from the inferior vena cava, and an intermediate external valve actuator with a proximal end portion and a distal end portion which is coupled to the intermediate external valve and which is adapted to adjust the intermediate external valve from the open position to the closed position.

10. The medical device assembly of claim 9, wherein the intermediate external valve further comprises an expandable member which is adjustable by said intermediate external valve actuator from a radially collapsed condition, which characterizes the open position for the intermediate external valve, to a radially expanded condition, which characterizes the closed position for the intermediate external valve.

11. The medical device assembly of claim 10, wherein the expandable member of the intermediate external valve further comprises an expandable balloon, and wherein the intermediate external valve actuator further comprises an intermediate valve actuating lumen which is adapted to fluidly couple the expandable balloon of the intermediate external valve's expandable member to a pressurizeable fluid source.

12. The medical device assembly of claim 9, wherein said elongate body further comprises a leakage port which is located along the elongate body between the intermediate external valve and the distal external valve and being in fluid communication with either the flow lumen or the intermediate flow lumen or a leakage flow lumen which extends along the elongate body between the leakage flow port and a third proximal flow port which is located along the proximal end portion of the elongate body and which is adapted to couple to an inlet port of a cardiopulmonary bypass pump.

13. The medical device assembly of claim 9, wherein said intermediate external valve actuator further comprises in-part said intermediate external valve actuator and also further comprises a distal external valve actuator which is coupled to the distal external valve.

14. The medical device assembly of claim 7, wherein said expandable member further comprises an expandable balloon, and wherein said external valve actuator further comprises an external valve actuating lumen which is adapted to fluidly couple the expandable balloon with a pressurizeable fluid source.

15. A method for performing a cardiac bypass procedure on a heart in a mammal, the heart comprising a right ventricle, a right atrium, and a sinus venarum through a superior vena cava and an inferior vena cava communicate with the right atrium, comprising:
    positioning an external valve, which is located on a distal end portion of a venous catheter, within a region of the superior and inferior vena cavae which is adjacent to the sinus venarum; and
    adjusting said external valve located on the distal end portion from an open position to a closed position which isolates the right ventricle from the vena cavae without circumferentially engaging an interior wall of the vena cavae.

16. The method of claim 15, further comprising:
    adjusting the external valve from a radially collapsed condition to a radially expanded condition which has an outer diameter that is smaller than an inner diameter of the interior wall of the vena cavae.

17. The method of claim 16, wherein the venous catheter further includes an internal flow lumen extending between a distal flow port located along the distal end portion distally of the external valve and a proximal flow port located along the venous catheter along a proximal end portion of the venous catheter, further comprising:
    coupling the proximal flow port to an inlet port of a cardiopulmonary bypass pump; and
    aspirating a volume of venous blood from the superior vena cavae, into the internal flow lumen through the distal flow port, proximally along the internal flow lumen, and out from the internal flow lumen through the proximal flow port, and into the inlet port of the cardiopulmonary bypass pump.

18. The method of claim 17, wherein the external valve further includes a valve member which is positioned at a discrete location along the circumference of the venous catheter, further comprising:
    positioning the discrete location of the valve member so that it is aligned with and adjacent to the sinus venarum; and
    adjusting the valve member from a first radial position to a radially displaced position which is at least in part within the right atrium and which at least in part characterizes the closed position for the external valve.

19. The method of claim 18, further comprising
    when the valve member is adjusted to the radially displaced position, farther adjusting the valve member from a radially collapsed condition to a radially expanded condition.

20. The method of claim 19, wherein the valve member further comprises two expandable members which are separated by a space, further comprising:
    positioning the two expandable members within the right ventricle and atrium, respectively, such that the tricuspid valve is located within the space; and
    expanding at least one of the two expandable members such that the space is narrowed and such that the tricuspid valve is engaged between the two expandable members to thereby isolate the right ventricle from the right atrium and also from the vena cavae.

21. A medical device assembly for selectively shunting antegrade blood flow from an aortic root in an aorta of an animal and into a proximal region of the aorta which is located proximally of the aortic root, the aorta further including an aortic wall, comprising:
    an elongate body with a proximal end portion, a distal end portion, and a flow lumen which extends between a distal flow port located along the distal end portion of the elongate body and an intermediate flow port located along the distal end portion of the elongate body proximally of the distal flow port such that the intermediate flow port is adapted to be positioned within the proximal region of the aorta when the distal flow port is positioned within the aortic root;
    an external shunt valve which is located along the elongate body between the proximal and distal flow ports, which includes an anchor and a funnel, and which is adjustable between an open position and a shunting position;
    an actuator with a proximal end portion and a distal end portion that is coupled to the external shunt valve, and which is adapted to selectively adjust the external shunt valve between the open and shunting positions such that in the open position the anchor and funnel are adapted to allow passage of the antegrade blood flow through an exterior space between the distal end portion of the elongate body and the aortic wall, and wherein in the shunting position the anchor is adapted to radially engage the aortic wall such that the distal end portion of the elongate body is secured at a predetermined location along the aorta, and the funnel is adapted to substantially shunt the antegrade blood flow from the aortic root, into the flow lumen through the distal flow port, out of the flow lumen through the intermediate flow port, and into the proximal region of the aorta while substantially isolating the antegrade blood flow from the exterior space;

said elongate body further comprising a proximal flow port located along the proximal end portion of said elongate body where said flow lumen communicates exteriorly of said elongate body;

a cannula member having a distal end, a proximate end, and an axis of elongation slidably carried at least in part within said flow lumen where said distal end is selectively positionable within said flow lumen;

an expandable valve member carried by said cannula member adjacent said distal end of said cannula member and so adapted to permit selective adjustment between respective open and closed positions whereby adjusting said expandable valve to the closed position when said expandable valve is positioned within said flow lumen between the distal end of said elongate member and said intermediate flow port, said intermediate flow port and said proximate flow port are in fluid communication and isolated from said distal flow port; and whereby adjusting said expandable valve to the closed position where said expandable valve is positioned within said flow lumen between said proximate flow port and said intermediate port, said intermediate port and said distal flow port are in fluid communication and isolated from said proximal flow port.

22. The medical device assembly of claim 21 further comprising:

a cardioplegia delivery member with a proximal end portion, a distal end portion, and a cardioplegia delivery lumen that extends between a distal cardioplegia port located along the distal end portion of the cardioplegia delivery member and a proximal cardioplegia port located along the proximal end portion of the cardioplegia delivery member, the proximal cardioplegia port being adapted to couple to a pressurizeable source of cardioplegia agent, and the distal cardioplegia port being adapted to deliver a cardioplegia agent, distally of the external shunt valve to thereby temporarily arrest the beating of the heart; and a ventricular venting member with a distal end portion that extends distally from the distal end portion of the elongate body and also with a proximal end portion which terminates proximally along the proximal end portion of the elongate body, the ventricular venting member also forming a vent lumen that extends between a distal vent port located along the distal end portion of the ventricular venting member and a proximal vent port located along the proximal end portion of the ventricular venting member, such that the distal vent port is adapted to be positioned within the left ventricle when the distal flow port is positioned within the aortic root, and wherein the proximal vent port is adapted to couple to a decompression pump such that fluid may be aspirated from the left ventricle through the vent lumen.

23. The medical device assembly of claim 22 further comprising:

a cardiopulmonary bypass machine having an outlet port for the delivery of oxygen-rich blood into the arterial circulation and an inlet port for receiving blood from venous circulation;

the outlet port of the cardiopulmonary bypass machine being coupled to the proximal flow port of the elongate body.

24. The medical device assembly of claim 23, further comprising:

a venous catheter with a venous cannula member having a proximal end portion, a distal end portion, and further forming a venous flow lumen extending between a distal venous flow port located along the distal end portion of the venous cannula member and a proximal venous flow port located along the proximal end portion of the venous cannula member;

the proximal venous flow port being coupled to the inlet port of the cardiopulmonary bypass machine, and wherein the distal end portion of the venous cannula member is adapted for percutaneous transluminal delivery into a superior vena cava at a region adjacent to a sinus venarum in a right atrium, and is also adapted to substantially aspirate a volume of blood from the superior vena cava and also from an inferior vena cava and into the venous flow lumen through the distal venous flow port.

25. The medical device assembly of claim 21 where said cannula member further comprises:

a cardioplegia delivery lumen that extends between a distal cardioplegia port located along the distal end portion of said cannula member and a proximal cardioplegia port located along said proximal end portion of said cannula member, the proximal cardioplegia being adapted to couple to a pressurizeable source of cardioplegia agent, and the distal cardioplegia port being adapted to deliver a cardioplegia agent, distally of the external shunt valve to thereby temporarily arrest the beating of the heart; and a vent lumen that extends between a distal vent port located along the distal end portion of said cannula member and a proximal vent port located along the proximal end portion of said cannula member, such that the distal vent port is adapted to be positioned within the left ventricle when the distal flow port is positioned within the aortic root, and wherein the proximal vent port is adapted to couple to a decompression pump such that fluid may be aspirated from the left ventricle through the vent lumen.

26. The medical device assembly of claim 25 further comprising:

a cardiopulmonary bypass machine having an outlet port for the delivery of oxygen-rich blood into the arterial circulation and an inlet port for receiving blood from venous circulation;

the outlet port of the cardiopulmonary bypass machine being coupled to the proximal flow port of the elongate body.

27. The medical device assembly of claim 26 further comprising:

a venous catheter with a venous cannula member having a proximal end portion, a distal end portion, and further forming a venous, flow lumen extending between a distal venous flow port located along the distal end portion of the venous cannula member and a proximal venous flow port located along the proximal end portion of the venous cannula member;

the proximal venous flow port being coupled to the inlet port of the cardiopulmonary bypass machine, and wherein the distal end portion of the venous cannula member is adapted for percutaneous transluminal delivery into a superior vena cava at a region adjacent to a sinus venarum in a right atrium, and is also adapted to substantially aspirate a volume of blood from the superior vena cava and also from an inferior vena cava and into the venous flow lumen through the distal venous flow port.

28. A medical device assembly for selectively shunting a volume of blood from an aortic root of an aorta in an animal and into the proximal region of the aorta, the aorta further including an aortic wall, comprising:

an elongate body with a proximal end portion, a distal end portion, and a flow lumen which extends between a distal flow port located along the distal end portion and an intermediate flow port located along the distal end portion proximally of said distal flow port;

a cannula member having a distal end and an axis of elongation slidably carried at least in part within said flow lumen where said distal end of said cannula member is selectively positionable within said flow lumen;

an expandable valve member carried by said cannula member selectively positionable within said flow lumen and so adapted to permit selective adjustment between respective open and closed positions, an expandable valve actuator coupled to said expandable valve member so constructed and adapted to selectively permit adjustment of said expandable valve member between the open and closed positions; such that when said expandable valve member is positioned within said flow lumen between said intermediate flow port and said proximal port and said expandable valve member is adjusted to the closed position; said distal flow port is in fluid communication with said intermediate port isolating said proximal port from fluid flow through said flow lumen, and where said expandable valve member is positioned between said intermediate port and said distal port, said intermediate and proximate port are in fluid communication when said expandable valve is adjusted to the closed position and said distal port is isolated from fluid flow within said flow lumen.

29. The medical device assembly of claim 28, further comprising:

a cardioplegia delivery member with a proximal end portion, a distal end portion, and a cardioplegia delivery lumen which extends between a distal cardioplegia port located along the cardioplegia delivery member's distal end portion and a proximal cardioplegia port located along the cardioplegia delivery member's proximal end portion, the proximal cardioplegia port being adapted to couple to a pressurizeable cardioplegia agent source such that a cardioplegia agent may be delivered through the cardioplegia delivery lumen, out the distal cardioplegia port, and into the aortic root to thereby temporarily arrest the beating of the heart; and a ventricular venting member which includes a distal end portion that extends from the elongate body distally from the distal flow port, a proximal end portion, and a vent lumen that extends between a distal vent port located along the ventricular venting member's distal end portion and a proximal vent port located along the ventricular venting member's proximal end portion, wherein the distal end portion of the ventricular venting member is adapted such that the distal vent port is positioned within the left ventricle when the distal flow port is positioned within the aortic root, and wherein the proximal vent port is adapted to couple to a decompression pump such that a volume of blood may be aspirated from the left ventricle, into the distal vent port, through the vent lumen, out the proximal vent port, and into the decompression pump.

30. The medical device assembly of claim 29 further comprising:

a cardiopulmonary bypass machine having an outlet port for the delivery of oxygen-rich blood into the arterial circulation and an inlet port for receiving blood from venous circulation;

the outlet port of the cardiopulmonary bypass machine being coupled to the proximal flow port of the elongate body.

31. The medical device assembly of claim 30, further comprising:

a venous catheter with a venous cannula member having a proximal end portion, a distal end portion, and further forming a venous flow lumen extending between a distal venous flow port located along the distal end portion of the venous cannula member and a proximal venous flow port located along the proximal end portion of the venous cannula member;

the proximal venous flow port being coupled to the inlet port of the cardiopulmonary bypass machine, and wherein the distal end portion of the venous cannula member is adapted for percutaneous transluminal delivery into a superior vena cava at a region adjacent to a sinus venarum in a right atrium, and is also adapted to substantially aspirate a volume of blood from the superior vena cava and also from an inferior vena cava and into the venous flow lumen through the distal venous flow port.

32. The medical device assembly of claim 28 where said cannula member further comprises:

a cardioplegia delivery lumen that extends between a distal cardioplegia port located along the distal end portion of said cannula member and a proximal cardioplegia port located along the proximal end portion of said cannula member, the proximal cardioplegia port being adapted to couple to a pressurizeable source of cardioplegia agent, and the distal cardioplegia port being adapted to deliver a cardioplegia agent, distally of the external shunt valve to thereby temporarily arrest the beating of the heart; and a vent lumen that extends between a distal vent port located alone the distal end portion of said cannula member and a proximal vent port located along the proximal end portion of said cannula member, such that the distal vent port is adapted to be positioned within the left ventricle when the distal flow port is positioned within the aortic root, and wherein the proximal vent port is adapted to couple to a decompression pump such that fluid may be aspirated from the left ventricle through the vent lumen.

33. The medical device assembly of claim 32, further comprising:

a venous catheter with a venous cannula member having a proximal end portion, a distal end portion, and further forming a venous flow lumen extending between a distal venous flow port located along the distal end portion of the venous cannula member and a proximal venous flow port located along the proximal end portion of the venous cannula member; the proximal venous flow port being coupled to the inlet port of the cardiopulmonary bypass machine, and wherein the distal end portion of the venous cannula member is adapted for percutaneous transluminal delivery into a superior vena cava at a region adjacent to a sinus venarum in a right atrium, and is also adapted to substantially aspirate a volume of blood from the superior vena cava and also from an inferior vena cava and into the venous flow lumen through the distal venous flow port.

* * * * *